US007825279B2

(12) United States Patent
Boykin et al.

(10) Patent No.: US 7,825,279 B2
(45) Date of Patent: Nov. 2, 2010

(54) FUSED RING DICATIONIC ANTI-PROTOZOAN AGENTS AND THEIR PRODRUGS

(75) Inventors: David W. Boykin, Atlanta, GA (US); Richard R. Tidwell, Pittsboro, NC (US); W. David Wilson, Atlanta, GA (US); Reto Brun, Basel (CH); Reem K. Arafa, Atlanta, GA (US); Chad E. Stephens, Villa Rica, GA (US)

(73) Assignees: The University of North Carolina at Chapel Hill, Chapel Hill, NC (US); Georgia State University Research Foundation, Inc., Atlanta, GA (US)

( * ) Notice: Subject to any disclaimer, the term of this patent is extended or adjusted under 35 U.S.C. 154(b) by 123 days.

(21) Appl. No.: 10/992,607

(22) Filed: Nov. 18, 2004

(65) Prior Publication Data

US 2005/0165044 A1    Jul. 28, 2005

Related U.S. Application Data

(60) Provisional application No. 60/525,018, filed on Nov. 24, 2003.

(51) Int. Cl.
| | | |
|---|---|---|
| C07C 279/18 | (2006.01) | |
| C07D 219/12 | (2006.01) | |
| C07D 213/06 | (2006.01) | |
| A61K 31/155 | (2006.01) | |
| A61K 31/235 | (2006.01) | |
| A61K 31/24 | (2006.01) | |
| A61K 31/44 | (2006.01) | |

(52) U.S. Cl. .................. 564/235; 564/229; 564/238; 546/106; 546/306; 560/8; 560/34; 514/297; 514/357; 514/533; 514/534; 514/633; 514/634

(58) Field of Classification Search .................. None
See application file for complete search history.

(56) References Cited

U.S. PATENT DOCUMENTS

| 1,374,695 A * | 4/1921 | Weiss et al. .................. 568/321 |
| 5,521,189 A | 5/1996 | Boykin et al. |
| 5,521,190 A | 5/1996 | Henrie, II et al. |
| 5,628,984 A | 5/1997 | Boucher, Jr. |
| 6,114,392 A | 9/2000 | Gilad et al. |

FOREIGN PATENT DOCUMENTS

| WO | WO96/40114 A | 12/1996 |
| WO | WO 96/40138 | 12/1996 |
| WO | WO 2005/025565 A1 | 3/2005 |

OTHER PUBLICATIONS

Database CAPLUS on STN, Acc. No. 1939:24095, King et al., Ann. Trop. Med. (1938), 32, p. 177-192 (abstract).*

Database CAPLUS on STN, Acc. No. 1982:217423, Ferranti et al., Farmaco, Edizione Scientifica (1982), 37(3), p. 199-204 (abstract).*

Database CAPLUS on STN, Acc. No. 1963:435458, Grinsteins et al., Latvijas PSR Zinatnu Akademijas Vestis, Kimijas Serija (1962), No. 4, p. 519-522 (abstract).*

International Search Report corresponding to PCT appl. No. PCT/US04/38896 dated May 13, 2005.

Written Opinion corresponding to PCT appl. No. PCT/US04/38896 dated May 13, 2005.

Ferranti et al., Database CAPLUS on STN, Acc. No. 1982:217423 "Amino Derivatives of 9H-Fluorene Farmaco", *Edizione Scientifica*, 37 (3): 199-204, 1982.

International Preliminary Report on Patentability corresponding to PCT application No. PCT/US2004/038896 dated Jun. 8, 2006.

Official Action Corresponding to Chinese Patent Application No. 200480034750.5 dated Nov. 9, 2007.

Brendle et al., "Antileishmanial Activities of Several Classes of Aromatic Dications," Antimicrobial Agents and Chemotherapy, vol. 46, No. 3, pp. 797-807 (Mar. 2002).

Tanious et al., "Sequence-dependent binding of bis-amidine carbazole dications to DNA," Eur. J. Biochem., vol. 268, pp. 3455-3464 (Feb. 2001).

Tanious et al., "Effects of Compound Structure on Carbazole Dication—DNA Complexes: Tests of the Minor-Groove Complex Models," Biochemistry, vol. 39, pp. 12091-12101 (2000).

Blagburn et al., "Comparative Efficacy Evaluation of Dicationic Carbazole Compounds, Nitazoxanide, and Paromomycin against Cryptosporidium parvum Infections in a Neonatal Mouse Model," Antimicrobial Agents and Chemotherapy, vol. 42, No. 11, pp. 2877-2882 (Nov. 1998).

Del Poeta et al., "In vitro Antifungal Activities of a Series of Dication-Substituted Carbazoles, Furans, and Benzimidazoles," Antimicrobial Agents and Chemotherapy, vol. 42, No. 10, pp. 2503-2510 (Oct. 1998).

Supplementary Partial European Search Report corresponding to an EP Application No. 04811591.9-1211 dated Jul. 25, 2007.

Patrick et al. Synthesis and anti-Pneumocystis carinii pneumonia activity of novel dicationic divenzothiophenes and orally active prodrugs. European Journal of Medicinal Chemistry, vol. 34, (1999), pp. 575-583.

Wang et al. Dicationic dibenzofuran derivatives as anti-Pneumocystis carinii pneumonia agents: synthesis, DNA binding affinity, and anti-P. carinii activity in an immunosuppressed rat model. European Journal of Medicinal Chemistry, vol. 34, (1999), pp. 215-224.

Patrick at al. Anti-Pneumocystis carinii pneumonia activity of dicationic carbazoles. European Journal of Medicinal Chemistry, vol. 32, (1997), pp. 781-793.

(Continued)

*Primary Examiner*—Brian J Davis
(74) *Attorney, Agent, or Firm*—Jenkins, Wilson, Taylor & Hunt, P.A.

(57) ABSTRACT

Novel fused ring dicationic anti-protozoan compounds. Representative protozoan species include but are not limited to *Trypanosoma brucei rhodesiense* (T.b.r.) and *Plasmodium falciparum*. Prodrugs of these compounds can be used as an oral treatment for malaria and human African trypanosomiasis.

122 Claims, No Drawings

OTHER PUBLICATIONS

Dardonville et al. Bisguanidine, Bis(2-aminoimidazoline), and polyamine derivatives as potent and selective chemotherapeutic agents aginst Trypanosoma brucei rhodesiense. Synthesis and in vitro evaluation. Journal of Medicinal Chemistry, vol. 47, (2004), pp. 2296-2307.

Official Action corresponding to Chinese Patent Application No. 200480034750.5 dated Apr. 3, 2009.

Apted, F.I.C., Present status of chemotherapy and chemopropylaxis of human trypanosomiasis in the Eastern Hemisphere. *Pharmacology Ther*. vol. 11, No. 2, pp. 391-413 (1980).

Bell, C.A., et al., Structure-Activity Relationships of Analogs of Pentamidine against Plasmodium falciparum and Leishmania mexicana amazonensis. *Antimicrobial Agents and Chemotherapy*. vol. 34, No. 7, pp. 1381-1386 (1990).

Bell, C.A., et al., Structure-Activity Relationships of Pentamidine Analogs against Giardia lamblia and Correlation of Antigiardial Activity with DNA-Binding Affinity. *Antimicrobial Agents and Chemotherapy*. vol. 35, No. 6, pp. 1099-1107 (1991).

Blagburn, B. L., et al., Inhibition of Cryptosporidium parvum in Neonatal Hsd: (ICR)BR Swiss Miceloy Polyether Ionophores and Aromatic Amidines. *Antimicrobial Agents and Chemotherapy*. vol. 35, No. 7, pp. 1520-1523 (1991).

Boykin, D.W., et al., 2,5-Bis[4-(N-alkylamidino)phenyl] furans as Anti-Pneumocystis carinii Agents. *Journal of Medicinal Chemistry*. vol. 41. pp. 124-129 (1998).

Boykin, D.W., et al., Dicationic Diarylfurans as Anti-Pneumocystis carinii Agents. *Journal of Medicinal Chemistry*. vol. 38. pp. 912-916 (1995).

Bryceson, A.D.M., et al., Visceral leishmaniasis unresponsive to antimonial drugs II. Responsive to high dosage sodium stibogluconate or prolonged treatment with pentamidine. *Transactions of the Royal Society of Tropical Medicine & Hygiene*. vol. 79, No. 5, pp. 705-714 (1985).

Das, B.P., et al., Synthesis and Antiprotozoal Activity of 2,5-Bis(4-guanylphenyl) furans. *Journal of Medicinal Chemistry*. vol. 20. pp. 531-536 (1977).

Del Poeta, M., et al., Structure-In Vitro Activity Relationships of Pentamidine Analogues and Dication-Substituted Bis-Benzimidazoles as New Antifungal Agents. *Antimicrobial Agents and Chemotherapy*. vol. 42, No. 10, pp. 2495-2502 (1998).

Del Poeta, M., et al., In-vitro activity of dicationic aromatic compounds and fluconazole against Cryptococcus neoformans and Candida spp. *Journal of Antimicrobial Chemotherapy*. vol. 44. pp. 223-228 (1999).

Francesconi, I., et al., 2,4-Diphenyl Furan Diamidines as Novel Anti-Pneumocystis carinii Pneumonia Agents. *Journal of Medicinal Chemistry*. vol. 42. pp. 2260-2265 (1999).

Fulton, J.D., The course of Plasmodium relictum infection in canaries and treatment of bird and monkey malaria with synthetic bases. *Annals of Tropical Medicine and Parasitology*. vol. 34. pp. 53-66 (1940).

Hughes, W.T., et al., Efficacy of Trimethoprim and sulfamethoxazole in the Prevention and Treatment of Pneumocystis carinii Pneumonitis. *Antimicrobial Agents and Chemotherapy*. vol. 5. pp. 289-293 (1974).

Ismail, M. et al., Synthesis and Antiprotozoal Activity of Aza-Analogues of Furamidine. *Journal of Medicinal Chemistry*. vol. 46 pp. 4761-4769 (2003).

Ivady, V.G., et al., Ein neues behandlungsverfahren der interstitiellen plasmazelligen pneumonie ruhgeborener mit funfwertigem stibium and aromatischen diamidinen. *Monatschr. Kinderheilkd.*, vol. 106, pp. 10-14 (1958).

Kirk, R., et al., The use of certain aromatic diamidines in the treatment of Kala-azar. *Annals of Tropical Medicine and Parasitology*. vol. 34. pp. 181-197 (1940).

Lindsay, D.S. et al., Activity of Pentamidine and Pentamidine Analogs against Toxoplasma gondii in cell cultures. *Antimicrobial Agents and Chemotherapy*. vol. 35. pp. 1914-1916 (1991).

Lourie, E.M. et al., Studies in chemotherapy: XXI. The trypanocidal action of certain aromatic diamidines. *Annals of Tropical Medicine and Parasitology*. vol. 33. pp. 289-304 (1939).

Lourie, E.M. et al., Studies in Chemotherapy: XXII. The Action of Certain Aromatic Diamidines on Babesia Canis Infections of Puppies. *Annals of Tropical Medicine and Parasitology*. vol. 33 pp. 305-312 (1939).

King, H., et al., "Studies in chemotherapy: XIX. Further report on new trypanocidal Substances," Annals of Tropical Medicine and Parasitology. vol. 32 pp. 177-192 (1938).

* cited by examiner

FUSED RING DICATIONIC ANTI-PROTOZOAN AGENTS AND THEIR PRODRUGS

CROSS REFERENCE TO RELATED APPLICATIONS

This application claims the benefit of and priority to U.S. Provisional Patent Application Ser. No. 60/525,018, filed Nov. 24, 2003, the disclosure of which is incorporated herein by reference in its entirety.

TECHNICAL FIELD

The presently disclosed subject matter relates to methods of combating microbial infections with dicationic compounds. More particularly, the presently disclosed subject matter relates to methods of combating microbial infections with fused ring dicationic compounds, and to the novel compounds themselves.

ABBREVIATIONS

δ=chemical shift
Ac=acetyl
AcO=acetoxyl
AcOH=acetic acid
$Ac_2O$=acetic anhydride
Am=amidine
AmOH=amidoxime
BOC=t-butoxycarbonyl
Bu=butyl
°C.=degrees Celsius
calcd=calculated
cm=centimeters
dec=decomposition point
DIBAL=diisobutylaluminium hydride
DMF=dimethylformamide
DMSO=dimethylsulfoxide
$D_2O$=deuterium oxide
EtOAc=ethyl acetate
EtOH=ethanol
FAB=fast atom bombardment
g=grams
h=hours
HCl=hydrogen chloride
HPLC=high-pressure liquid chromatography
Hz=hertz
kg=kilograms
KO-t-Bu=potassium tert-butoxide
L. d.=*Leishmania donovani*
M=molar
Me=methyl
MeO=methoxyl
MHz=megahertz
mL=milliliters
mm=millimeters
mM=millimolar
m.p.=melting point
MS=mass spectroscopy
$Na_2CO_3$=sodium carbonate
$Na_2SO_4$=sodium sulfate
NBS=N-bromosuccinimide
$NH_2OH.HCl$=hydroxylamine hydrochloride
NMR=nuclear magnetic resonance
p=para
Pd—C=10% palladium on carbon
P. f.=*Plasmodium falciparum*
psi=pounds per square inch
spp.=species
T. br.=*Trypanosoma brucei rhodesiense*
THF=tetrahydrofuran
TLC=thin-layer chromatography
TMS=trimethylsilyl
UV=ultraviolet

BACKGROUND

The incidence of microbial infections (e.g., mycobacterial, fungal, and protozoal infections) in the immunocompromised population has significantly increased over the past several years. In particular, *Candida* species, especially *Candida albicans*, are often significant pathogens in patients infected with human immunodeficiency virus (HIV). Another pathogen, *Pneumocystis carinii*, causes a form of pneumonia (PCP) that is believed to be one of the leading causes of death in patients suffering from AIDS. Further, Human African trypanosomiasis (HAT) has reemerged as a threat to over 60 million people. Current estimates are that between 350,000 and 450,000 people are infected. Other severe and life-threatening microbial infections are caused by *Mycobacterium tuberculosis*, *Aspergillus* spp., *Cryptosporidium parvum*, *Giardia lamblia*, *Plasmodium* spp., *Toxoplasma gondii*, *Fusarium solani*, and *Cryptococcus neoformans*.

The antimicrobial properties of dicationic molecules have been studied since the 1930's. Compounds of this type have typically utilized amidine groups as the cationic moieties, and their activities against a number of pathogens including *Cryptosporidium parvum*, *Giardia lamblia*, *Leishmania* spp., *Plasmodium* spp., *Pneumocystis carinii*, *Toxoplasma gondii*, *Trypanosoma* spp., *Candida albicans*, *Aspergillus* spp. and *Cryptococcus neoformans* have been reported. See, e.g., King, H. et al., *Ann. Trop. Med. Parasitol.* 1938, 32, 177-192; Blaqburn, B. L. et al., *Antimicrob. Agents Chemother.* 1991, 35, 1520-1523; Bell, C. A. et al., *Antimicrob. Agents Chemother.* 1991, 35, 1099-1107; Bell, C. A. et al., *Antimicrob. Agents Chemother.* 1990, 34, 1381-1386; Kirk, R. et al., *Ann. Trop. Med. Parasitol.* 1940, 34,181-197; Fulton, J. D. *Ann. Trop. Med. Parasitol.* 1940, 34, 53-66; Ivady, V. G. et al., *Monatschr. Kinderheilkd.* 1958, 106, 10-14; Bovkin, D. W. et al., *J. Med. Chem.* 1995, 38, 912-916; Boykin, D. W. et al., *J. Med. Chem.* 1998, 41, 124-129; Francesconi, I. et al., *J. Med. Chem.* 1999, 42, 2260-2265; Lindsay, D. S. et al., *Antimicrob. Agents Chemother.* 1991, 35, 1914-1916; Lourie, E. M. et al., *Ann. Trop. Med. Parasitol.* 1939, 33, 289-304; Lourie, E. M. et al., *Ann. Trop. Med. Parasitol.* 1939, 33, 305-312; Das, B. P. et al., *J. Med. Chem.* 1976, 20, 531-536; Del Poeta, M. et al., *J. Antimicrob. Chemother.* 1999, 44, 223-228; Del Poeta, M. et al., *Antimicrob. Agents Chemother.* 1998, 42, 2495-2502; Del Poeta, M. et al., *Antimicrob. Agents Chemother.* 1998, 42, 2503-2510.

Despite the broad range of activity exhibited by diamidines, only one compound of this chemical type, pentamidine, has seen significant clinical use. Pentamidine has been used clinically against African trypanosomiasis, antimony-resistant leishmaniasis, and *P. carinii* pneumonia. See, e.g., Apted, F.I.C., *Pharmacol. Ther.* 1980, 11, 391-413; Bryceson, A. D. M. et al., *Trans. Roy. Soc. Trop. Med. Hyg.* 1985, 79, 705-714; Hughes, W. T. et al., *Antimicrob. Agents Chemother.* 1974, 5, 289-293.

Thus, there is a need for compounds having antimicrobial activity, whether against the representative pathogens referenced above or against other pathogens. More particularly, there is a need for a compound having activity in the treatment of human African trypanosomiasis, an infectious disease for which oral treatment in its second stage is not currently available.

SUMMARY

The presently disclosed subject matter describes a compound of Formula I:

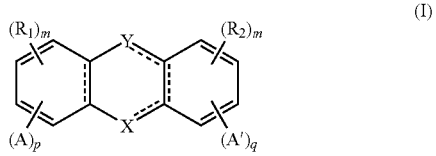

wherein:
X and Y are each independently selected from the group consisting of CH, $CH_2$, N, C=O, O, S, and $NR_3$,
wherein $R_3$ is selected from the group consisting of H, alkyl, aryl, alkoxyl, and aryloxyl, and
Y can be present or absent;
$R_1$ and $R_2$ are each independently selected from the group consisting of H, alkyl, halo, hydroxyl, alkoxyl, aryloxyl, and aralkyloxyl;
m and n are integers from 0 to 3, provided that when m is zero, $R_1$ is an implied hydrogen, and when n is zero, $R_2$ is an implied hydrogen;
p and q are integers from 0 to 1;
A and A' are each independently selected from one of:

wherein:
$R_4$, $R_5$, $R_6$, $R_7$, and $R_5$ are each independently selected from the group consisting of H, alkyl, cycloalkyl, aryl, aralkyl, hydroxyl, alkoxyl, hydroxyalkyl, hydroxycycloalkyl, alkoxycycloalkyl, am inoa lkyl, acyloxyl, alkylaminoalkyl, and alkoxycarbonyl; or
$R_5$ and $R_6$ together represent a $C_2$ to $C_{10}$ alkyl, hydroxyalkyl, or alkylene; or
$R_8$ is

wherein:
$R_9$ and $R_{10}$ are each independently selected from the group consisting of H, alkyl, aryl, and $-OR_{11}$;
wherein:
$R_{11}$ is selected from the group consisting of H, alkyl, and aryl.
In some embodiments, the presently disclosed subject matter relates to a pharmaceutical formulation comprising a compound of Formula I in a pharmaceutically acceptable carrier.

In some embodiments, the presently disclosed subject matter relates to a method of treating a microbial infection, comprising administering an effective amount of a compound of Formula I to a subject in need thereof.

In some embodiments, the presently disclosed subject matter relates to the use of an active compound as described hereinabove (i.e., a compound of Formula I) for the preparation of a medicament for treating a microbial infection.

Accordingly, in some embodiments, the presently disclosed subject matter provides compounds that are useful in the treatment of microbial infections. In some embodiments, the presently disclosed subject matter provides pharmaceutical formulations for use in the treatment of microbial infections. In some embodiments, the presently disclosed subject matter provides methods for treating microbial infections.

Certain embodiments of the presently disclosed subject matter having been stated hereinabove, which are addressed in whole or in part by the presently disclosed subject matter, other embodiments will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), i.e., 1, 2, 3, 4, 5, 6, 7, or 8 carbon atoms. "Higher alkyl" refers to an alkyl group having about 10 to about 20 carbon atoms, i.e., 10, 11, 12, 13, 14, 15, 16, 17, 18, 19, or 20 carbon atoms (i.e., a $C_{10-20}$ alkyl). In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can be optionally substituted with one or more alkyl group substituents, which can be the same or different. The term "alkyl group substituent" includes but is not limited to alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

The term "aryl" is used herein to refer to an aromatic substituent that can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In some embodiments, the term "aryl" means a cyclic aromatic comprising from about 5 to about 10 carbon atoms, i.e., 5, 6, 7, 8, 9, or 10 carbon atoms, and including 5- and 6-membered hydrocarbon and heterocyclic aromatic rings.

The aryl group can be optionally substituted with one or more aryl group substituents which can be the same or different, wherein "aryl group substituent" includes alkyl, aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can be each independently hydrogen, alkyl, aryl, and aralkyl.

Specific examples of aryl groups include but are not limited to cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A dashed line representing a bond in an aryl group indicates that the bond is either present or absent depending on the number of atoms comprising the aromatic ring and, in the case of a heterocyclic aromatic ring, the identity of the heteroatom.

When a named atom of an aromatic ring or a heterocyclic aromatic ring is defined as being "absent," the named atom is replaced by a direct bond.

As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxyl, hydroxyl, nitro, amino, alkylamino, dialkylamino, sulfate, and mercapto.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups. Specific examples of acyl groups include acetyl and benzoyl.

"Cyclic" and "cycloalkyl" refer to a non-aromatic mono- or multi-cyclic ring system of about 3 to about 10 carbon atoms, i.e., 3, 4, 5, 6, 7, 8, 9, or 10 carbon atoms. The cycloalkyl group can be optionally partially unsaturated. The cycloalkyl group can be also optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, lower alkyl, or aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described. The term "aryloxyl" as used herein can refer to phenyloxyl or hexyloxyl, and alkyl, halo, or alkoxyl substituted phenyloxyl or hexyloxyl.

"Aralkyl" refers to an aryl-alkyl-group wherein aryl and alkyl are as previously described. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group as previously described. Exemplary alkylamino groups include ethylmethylamino, dimethylamino, and diethylamino.

"Alkoxycarbonyl" refers to an alkyl-O—C(=O) group. Exemplary alkoxycarbonyl groups include methoxycarbonyl, ethoxycarbonyl, butyloxycarbonyl, and t-butyloxycarbonyl. An alkoxycarbonyl group can be further represented by the following structural formula:

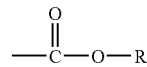

wherein the "R" group represents an alkyl group as defined hereinabove. An alkoxycarbonyl group also can be referred to as an "alkyl ester" group. In some embodiments of the presently disclosed subject matter, R is an ethyl group and the alkoxycarbonyl group comprises the following formula:

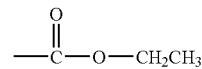

"Aryloxycarbonyl" refers to an aryl-O—C(=O) group. Exemplary aryloxycarbonyl groups include phenoxy- and naphthoxy-carbonyl.

"Aralkoxycarbonyl" refers to an aralkyl-O—C(=O) group. An exemplary aralkoxycarbonyl group is benzyloxycarbonyl.

"Carbamoyl" refers to an $H_2N$—C(=O) group.

"Alkylcarbamoyl" refers to a R'RN—C(=O) group wherein one of R and R' is hydrogen and the other of R and R' is alkyl as previously described.

"Dialkylcarbamoyl" refers to R'RN—C(=O) group wherein each of R and R' is independently alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

"Alkylene" refers to a straight or branched bivalent aliphatic hydrocarbon group having from 1 to about 20 carbon atoms, i.e., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)(CH$_2$)$_r$—, wherein each of q and r is independently an integer from 0 to about 20, i.e., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

The term "amino" refers to the —NH$_2$ group.
The term "carbonyl" refers to the —(C=O)— group.
The term "carboxyl" refers to the —C(=O)OH group.
The terms "halo", "halide", or "halogen" as used herein refer to fluoro, chloro, bromo, and iodo groups.
The term "hydroxyl" refers to the —OH group.
The term "hydroxyalkyl" refers to an alkyl group substituted with an —OH group.
The term "mercapto" refers to the —SH group.
The term "oxo" refers to a compound described previously herein wherein a carbon atom is replaced by an oxygen atom.
The term "nitro" refers to the —NO$_2$ group.
The term "thio" refers to a compound described previously herein wherein a carbon or oxygen atom is replaced by a sulfur atom.
The term "sulfate" refers to the —SO$_4$ group.

When the term "independently selected" is used, the substituents being referred to (i.e., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "R'," "X," "Y," "Y'", "A," "A'", "B," "L," or "Z" group generally will have the structure that is recognized in the art as corresponding to a group having that name, unless specified otherwise herein. For the purposes of illustration, certain representative "R," "X," "Y", and "A" groups as set forth above are defined below. These definitions are intended to supplement and illustrate, not preclude, the definitions that would be apparent to one of ordinary skill in the art upon review of the present disclosure.

II. Novel Compounds

A. Compounds of Formula I

In some embodiments, the presently disclosed subject matter provides a compound of Formula I:

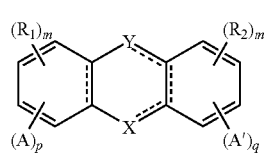

(I)

wherein:
X and Y are each independently selected from the group consisting of CH, CH$_2$, N, C=O, O, S, and NR$_3$, wherein $R_3$ is selected from the group consisting of H, alkyl, aryl, alkoxyl, and aryloxyl, and
Y can be present or absent;

$R_1$ and $R_2$ are each independently selected from the group consisting of H, alkyl, halo, hydroxyl, alkoxyl, aryloxyl, and aralkyloxyl;

m and n are integers from 0 to 3, provided that when m is zero, $R_1$ is an implied hydrogen, and when n is zero, $R_2$ is an implied hydrogen;

p and q are integers from 0 to 1;

A and A' are each independently selected from one of:

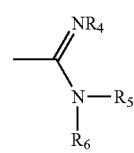 and 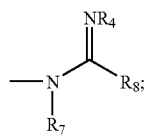

wherein:
$R_4$, $R_5$, $R_6$, $R_7$, and $R_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_5$ and $R_6$ together represent a $C_2$ to $C_{10}$ alkyl, hydroxyalkyl, or alkylene; or $R_8$ is

wherein:
$R_9$ and $R_{10}$ are each independently selected from the group consisting of H, alkyl, aryl, and —OR$_{11}$;
wherein:
$R_{11}$ is selected from the group consisting of H, alkyl, and aryl.

In some embodiments of the compound of Formula I, X is CH$_2$ and Y is absent. In such embodiments, the fused-ring structure comprises 9H-fluorene. In some embodiments, A and A' are each independently

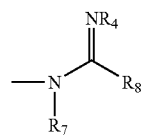

wherein:
p and q are each 1;
$R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and $R_8$ is selected from the group consisting of aryl and

wherein:
$R_9$ and $R_{10}$ are each independently selected from the group consisting of H, alkyl, aryl, and $-OR_{11}$;
wherein:
$R_{11}$ is selected from the group consisting of H, alkyl, and aryl.

In some embodiments, A and A' are in the 2- and 7-positions of the 9H-fluorene ring.

In some embodiments, m and n are both zero and $R_7$ is H. In some embodiments, $R_4$ is H and $R_8$ is phenyl. In some embodiments, $R_4$ is H and $R_8$ is 2-pyridyl.

In some embodiments, $R_8$ is

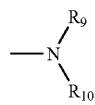

wherein:
$R_9$ and $R_{10}$ are each independently selected from the group consisting of H, alkyl, aryl, and $-OR_{11}$; and
wherein:
$R_{11}$ is selected from the group consisting of H, alkyl, and aryl.

In some embodiments, $R_4$ and $R_9$ are each H. In some embodiments, $R_4$ is ethoxycarbonyl and $R_9$ is H. In some embodiments, $R_{10}$ is H. In some embodiments, $R_{10}$ is methyl. In some embodiments, $R_{10}$ is isopropyl. In some embodiments, $R_{10}$ is methoxyl. In some embodiments, $R_{10}$ is isobutoxyl.

In some embodiments of the compound of Formula I, X is C=O and Y is absent. In such embodiments, the fused-ring structure comprises 9H-fluoren-9-one. In some embodiments, A and A' are each independently

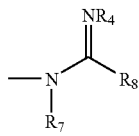

wherein:
p and q are each 1;
$R_4$ and $R_7$ are each independently selected from the group consisting of H alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and $R_8$ is selected from the group consisting of aryl and

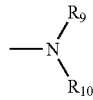

wherein:
$R_9$ and $R_{10}$ are each independently selected from the group consisting of H, alkyl, aryl, and $-OR_{11}$; and
wherein:
$R_{11}$ is selected from the group consisting of H, alkyl, and aryl.

In some embodiments, A and A' are in the 2- and 7-positions of the 9H-fluoren-9-one ring. In some embodiments, m and n are both zero and $R_7$ is H. In some embodiments, $R_8$ is

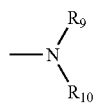

wherein:
$R_9$ and $R_{10}$ are each independently selected from the group consisting of H, alkyl, aryl, and $-OR_{11}$;
wherein:
$R_{11}$ is selected from the group consisting of H, alkyl, and aryl.

In some embodiments, $R_9$ and $R_{10}$ are both H. In some embodiments, $R_4$ is H. In some embodiments, $R_4$ is ethoxycarbonyl.

In some embodiments of the compound of Formula I, X and Y are both C=O. In such embodiments, the fused-ring structure comprises 9,10-anthraquinone. In some embodiments, A and A' are each independently

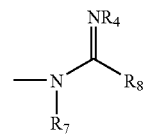

wherein:
p and q are each 1;
$R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
$R_8$ is selected from the group consisting of aryl and

wherein:
$R_9$ and $R_{10}$ are each independently selected from the group consisting of H, alkyl, aryl, and $-OR_{11}$;

wherein:
$R_{11}$ is selected from the group consisting of H, alkyl, and aryl.

In some embodiments, m and n are both zero and $R_7$ is H. In some embodiments, $R_8$ is

wherein:
$R_9$ and $R_{10}$ are each independently selected from the group consisting of H, alkyl, aryl, and $-OR_{11}$;
wherein:
$R_{11}$ is selected from the group consisting of H, alkyl, and aryl.

In some embodiments, $R_9$ and $R_{10}$ are both H. In some embodiments, $R_4$ is H.

In some embodiments of the compounds of Formula I, X is N and Y is CH. In such embodiments, the fused-ring structure comprises acridine. In some embodiments, A and A' are each independently

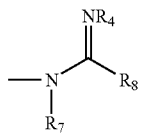

wherein:
p and q are each 1;
$R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
$R_8$ is selected from the group consisting of aryl and

wherein:
$R_9$ and $R_{10}$ are each independently selected from the group consisting of H, alkyl, aryl, and $-OR_{11}$; and
wherein:
$R_{11}$ is selected from the group consisting of H, alkyl, and aryl.

In some embodiments, A and A' are in the 3- and 6-positions of the acridine ring. In some embodiments, m and n are both zero and $R_7$ is H. In some embodiments, $R_8$ is

wherein:
$R_9$ and $R_{10}$ are each independently selected from the group consisting of H, alkyl, aryl, and $-OR_{11}$; and
wherein:
$R_{11}$ is selected from the group consisting of H, alkyl, and aryl.

In some embodiments, $R_9$ and $R_{10}$ are both H. In some embodiments, $R_4$ is H.

In some embodiments of the compound of Formula I, the compound is selected from the group consisting of: 2,7-bis-guanidino-9H-fluorene; 2,7-bis-guanidinofluoren-9-one; 2,7-bis-guanidinoanthraquinone; 3,6-bis-guanidinoacridine; 2,7-bis-(N"-ethoxycarbonyl)guanidino-9H-fluorene; 2,7-bis (N"-ethoxycarbonyl)guanidinofluoren-9-one; 2,7-bis(N"-ethoxycarbonyl-N'-methyl)guanidino-9H-fluorene; 2,7-bis (N"-ethoxycarbonyl-N'-isopropyl)guanidino-9H-fluorene; 2,7-bis(N"-ethoxycarbonyl-N'-methoxy)guanidino-9H-fluorene; 2,7-bis(N"-ethoxycarbonyl-N'-isobutoxy)guanidine-9H-fluorene; 2,7-bis(N'-methyl)guanidino-9H-fluorene; 2,7-bis(N'-iso-propyl)guanidino-9H-fluorene; 2,7-bis(N'-methoxy)guanidino-9H-fluorene; 2,7-bis(N'-isobutoxy) guanidine-9H-fluorene; 2,7-bis[(phenylimino)amino)]-9H-fluorene; and 2,7-bis[(2-pyridylimino)amino)-9H-fluorene.

In some embodiments, the compound of Formula I comprises a pharmaceutically acceptable salt. In some embodiments, the salt is a hydrochloride salt.

B. Prodrugs

In representative embodiments, compounds disclosed herein are prodrugs. A prodrug means a compound that, upon administration to a recipient, is capable of providing (directly or indirectly) a compound of this presently disclosed subject matter or an inhibitorily active metabolite or residue thereof. Prodrugs can increase the bioavailability of the compounds of the presently disclosed subject matter when such compounds are administered to a subject (e.g., by allowing an orally administered compound to be more readily absorbed into the blood) or can enhance delivery of the parent compound to a biological compartment (e.g., the brain or lymphatic system) relative to a metabolite species, for example. A number of the compounds (e.g., compounds 7a, 7b, 7c, 7d, 8c, and 10) discussed in Example 2 are prodrugs.

C. Pharmaceutically Acceptable Salts

Additionally, the active compounds of the presently disclosed subject matter can be administered as pharmaceutically acceptable salts. Such salts include the gluconate, lactate, acetate, tartarate, citrate, phosphate, borate, nitrate, sulfate, and hydrochloride salts. The salts of the compounds described herein can be prepared, in general, by reacting two equivalents of the base compound with the desired acid, in solution. After the reaction is complete, the salts are crystallized from solution by the addition of an appropriate amount of solvent in which the salt is insoluble. In some embodiments, the pharmaceutically acceptable salt is a hydrochloride salt.

III. Pharmaceutical Formulations

The compounds of Formula I, the pharmaceutically acceptable salts thereof, prodrugs corresponding to compounds of Formula I, and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, or aerosol administration as described in greater detail herein below. Also, the presently disclosed subject matter provides such active compounds that have been lyophilized and that can be reconstituted to form pharmaceutically acceptable formulations for administration, as by intravenous or intramuscular injection.

The therapeutically effective dosage of any specific active compound, the use of which is in the scope of embodiments described herein, will vary somewhat from compound to compound, and patient to patient, and will depend upon the condition of the patient and the route of delivery. As a general proposition, a dosage from about 0.1 mg/kg to about 50 mg/kg will have therapeutic efficacy, with all weights being calculated based upon the weight of the active compound, including the cases where a salt is employed. Toxicity concerns at the higher level can restrict intravenous dosages to a lower level such as up to about 10 mg/kg, with all weights being calculated based upon the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. In some embodiments, dosages range from between 1 µmol/kg to 50 µmol/kg of the compound for intravenous or oral administration. In some embodiments, dosages range from between 22 µmol/kg and 33 µmol/kg of the compound for intravenous or oral administration. The duration of the treatment typically is once per day for a period of two to three weeks or until the condition is essentially controlled. Lower doses given less frequently can be used prophylactically to prevent or reduce the incidence of recurrence of the infection.

In accordance with the presently disclosed methods, pharmaceutically active compounds as described herein can be administered orally as a solid or as a liquid, or can be administered intramuscularly or intravenously as a solution, suspension, or emulsion. Alternatively, the compounds or salts can be administered by inhalation, intravenously or intramuscularly as a liposomal suspension. When administered through inhalation the active compound or salt should be in the form of a plurality of solid particles or droplets having, in some embodiments, a particle size from about 0.5 microns to about 5 microns, and in some embodiments, a particle size from about 1 micron to about 2 microns.

Pharmaceutical formulations suitable for intravenous or intramuscular injection are further embodiments provided herein. The pharmaceutical formulations comprise a compound of Formula I described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. Of course, the dispensing is preferably done by an aseptic method. Sterilized closures can then be placed on the vials and, if desired, the vial contents can be lyophilized.

In addition to compounds of Formula I or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain anti-microbial preservatives. Useful anti-microbial preservatives include methylparaben, propylparaben, and benzyl alcohol. The anti-microbial preservative is typically employed when the formulation is placed in a vial designed for multi-dose use. The pharmaceutical formulations described herein can be lyophilized using techniques well known in the art.

In some embodiments of the subject matter described herein, there is provided an injectable, stable, sterile formulation comprising a compound of Formula I, or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines, and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations containing the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol, by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. In some embodiments, the liquid droplets or solid particles have a particle size in the range of about 0.5 microns to about 10 microns. In some embodiments, the liquid droplets or solid particles have a particle size in the range of about 0.5 to about 5 microns. The solid particles can be obtained by processing the solid compound or a salt thereof, in any appropriate manner known in the art, such as by micronization. In some embodiments, the size of the solid particles or droplets will be from about 1 micron to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided by the presently disclosed subject matter. As used in the presently disclosed subject matter, the term "water-soluble" is meant to define any composition that is soluble in water in an amount of about 50 mg/mL, or greater. Also, as used in the presently disclosed subject matter, the term "water-insoluble" is meant to define any composition that has solubility in water of less than about 20 mg/mL. For certain applications, water-soluble compounds or salts can be desirable whereas for other applications water-insoluble compounds or salts likewise can be desirable.

Accordingly, in some embodiments, the presently disclosed subject matter provides a pharmaceutical formulation comprising:
(a) a pharmaceutically acceptable carrier; and
(b) a compound of Formula I:

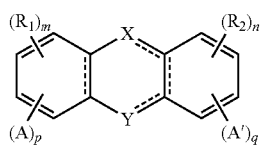

(I)

wherein:
X and Y are each independently selected from the group consisting of CH, $CH_2$, N, C=O, O, S, and $NR_3$,
    wherein $R_3$ is selected from the group consisting of H, alkyl, aryl, alkoxyl, and aryloxyl, and
    Y can be present or absent;
$R_1$ and $R_2$ are each independently selected from the group consisting of H, alkyl, halo, hydroxyl, alkoxyl, aryloxyl, and aralkyloxyl;
m and n are integers from 0 to 3, provided that when m is zero, $R_1$ is an implied hydrogen, and when n is zero, $R_2$ is an implied hydrogen;
p and q are integers from 0 to 1;
A and A' are each independently selected from one of:

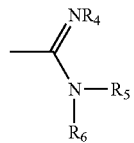 and 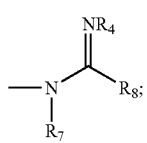

wherein:
$R_4$, $R_5$, $R_6$, $R_7$, and $R_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_5$ and $R_6$ together represent a $C_2$ to $C_{10}$ alkyl, hydroxyalkyl, or alkylene; or
$R_8$ is

wherein:
$R_9$ and $R_{10}$ are each independently selected from the group consisting of H, alkyl, aryl, and $—OR_{11}$; and
wherein:
$R_{11}$ is selected from the group consisting of H, alkyl, and aryl;

or a pharmaceutically acceptable salt thereof.

In some embodiments of the pharmaceutical formulation of a compound of Formula I, X is $CH_2$ and Y is absent. In such embodiments, the fused-ring structure comprises 9H-fluorene. In some embodiments, A and A' are each independently

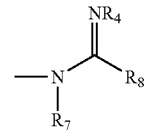

wherein:
p and q are each 1;
$R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
$R_8$ is selected from the group consisting of aryl and

wherein:
$R_9$ and $R_{10}$ are each independently selected from the group consisting of H, alkyl, aryl, and $—OR_{11}$;
wherein:
$R_{11}$ is selected from the group consisting of H, alkyl, and aryl.

In some embodiments, A and A' are in the 2- and 7-positions of the 9H-fluorene ring.

In some embodiments, m and n are both zero and $R_7$ is H. In some embodiments, $R_4$ is H and $R_8$ is phenyl. In some embodiments, $R_4$ is H and $R_8$ is 2-pyridyl.

In some embodiments, $R_8$ is

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

In some embodiments, $R_4$ and $R_9$ are each H. In some embodiments, $R_4$ is ethoxycarbonyl and $R_9$ is H. In some embodiments, $R_{10}$ is H. In some embodiments, $R_{10}$ is methyl. In some embodiments, $R_{10}$ is isopropyl. In some embodiments, $R_{10}$ is methoxyl. In some embodiments, $R_{10}$ is isobutoxyl.

In some embodiments of the pharmaceutical formulation of a compound of Formula I, X is C=O and Y is absent. In such embodiments, the fused-ring structure comprises 9H-fluoren-9-one. In some embodiments, A and A' are each independently

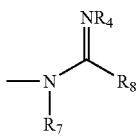

wherein:
p and q are each 1;
$R_4$ and $R_7$ are each independently selected from the group consisting of H alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
$R_8$ is selected from the group consisting of aryl and

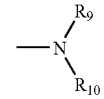

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

In some embodiments, A and A' are in the 2- and 7-positions of the 9H-fluoren-9-one ring. In some embodiments, m and n are both zero; and $R_7$ is H. In some embodiments, $R_8$ is

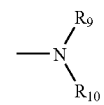

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

In some embodiments, $R_9$ and $R_{10}$ are both H. In some embodiments, $R_4$ is H. In some embodiments, $R_4$ is ethoxycarbonyl.

In some embodiments of the pharmaceutical formulation of a compound of Formula I, X and Y are both C=O. In such embodiments, the fused-ring structure comprises 9,10-anthraquinone. In some embodiments, A and A' are each independently

wherein:
p and q are each 1;
$R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
$R_8$ is selected from the group consisting of aryl and

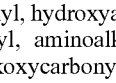

wherein:
$R_9$ and $R_{10}$ are each independently selected from the group consisting of H, alkyl, aryl, and —$OR_{11}$;
wherein:
$R_{11}$ is selected from the group consisting of H, alkyl, and aryl.

In some embodiments, m and n are both zero and $R_7$ is H. In some embodiments, $R_8$ is

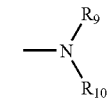

wherein:
$R_9$ and $R_{10}$ are each independently selected from the group consisting of H, alkyl, aryl, and —$OR_{11}$;
wherein:
$R_{11}$ is selected from the group consisting of H, alkyl, and aryl.

In some embodiments, $R_9$ and $R_{10}$ are both H. In some embodiments, $R_4$ is H.

In some embodiments of the pharmaceutical formulation of a compound of Formula I, X is N and Y is CH. In such embodiments, the fused-ring structure comprises acridine. In some embodiments, A and A' are each independently

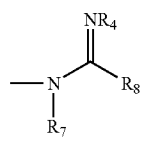

wherein:
p and q are each 1;
$R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
$R_8$ is selected from the group consisting of aryl and

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

In some embodiments, A and A' are in the 3- and 6-positions of the acridine ring. In some embodiments, m and n are both zero; and $R_7$ is H. In some embodiments, $R_8$ is

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

In some embodiments, $R_9$ and $R_{10}$ are both H. In some embodiments, $R_4$ is H.

In some embodiments of the pharmaceutical formulation of a compound of Formula I, the compound is selected from the group consisting of: 2,7-bis-guanidino-9H-fluorene; 2,7-bis-guanidinofluoren-9-one; 2,7-bis-guanidinoanthraquinone; 3,6-bis-guanidinoacridine; 2,7-bis-(N''-ethoxycarbonyl)guanidino-9H-fluorene; 2,7-bis(N''-ethoxycarbonyl)guanidinofluoren-9-one; 2,7-bis(N''-ethoxycarbonyl-N'-methyl)guanidino-9H-fluorene; 2,7-bis(N''-ethoxycarbonyl-N'-isopropyl)guanidino-9H-fluorene; 2,7-bis(N''-ethoxycarbonyl-N'-methoxy)guanidino-9H-fluorene; 2,7-bis(N''-ethoxycarbonyl-N'-isobutoxy)guanidine-9H-fluorene; 2,7-bis(N'-methyl)guanidino-9H-fluorene; 2,7bis(N'-iso-propyl)guanidino-9H-fluorene; 2,7-bis(N'-methoxy)guanidino-9H-fluorene; 2,7-bis(N'-isobutoxy) guanidine-9H-fluorene; 2,7-bis[(phenylimino)amino)]-9H-fluorene; and 2,7-bis[(2-pyridylimino)amino)-9H-fluorene.

IV. Methods Of Treating Microbial Infections

Subjects with microbial infections can be treated by methods described herein. These infections can be caused by a variety of microbes, including fungi, algae, protozoa, bacteria, and viruses. Exemplary microbial infections that can be treated by the method of the presently disclosed subject matter include, but are not limited to, infections caused by *Trypanosoma* species (e.g., *Trypanosoma brucei rhodesiense*), *Pneumocytsis carnii*, *Giardia lamblia*, *Cryptosporidium parvum*, *Cryptococcus neoformans*, *Candida albicans*, *Candida tropicalis*, *Salmonella typhimurium*, *Plasmodium falciparum*, *Leishmania donovani*, and *Leishmania mexicana amazonensis*. The methods of the presently disclosed subject matter are useful for treating these conditions in that they inhibit the onset, growth, or spread of the condition, cause regression of the condition, cure the condition, or otherwise improve the general well-being of a subject afflicted with, or at risk of contracting the condition.

Methods of treating microbial infections comprise administering to a subject in need of treatment an active compound as described herein. These active compounds, as set forth above, include compounds of Formula I, their corresponding prodrugs, and pharmaceutically acceptable salts of the compounds and prodrugs.

With regard to the presently described method embodiments, compounds of Formula I are defined as having a structure as follows:

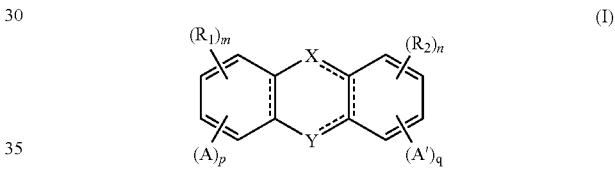

(I)

wherein:
X and Y are each independently selected from the group consisting of CH, $CH_2$, N, C=O, O, S and $NR_3$,
wherein $R_3$ is selected from the group consisting of H, alkyl, aryl, alkoxyl, and aryloxyl, and
Y can be present or absent;
$R_1$ and $R_2$ are each independently selected from the group consisting of H, alkyl, halo, hydroxyl, alkoxyl, aryloxyl, and aralkyloxyl;
m and n are integers from 0 to 3, provided that when m is zero, $R_1$ is an implied hydrogen, and when n is zero, $R_2$ is an implied hydrogen;
p and q are integers from 0 to 1;
A and A' are each independently selected from one of:

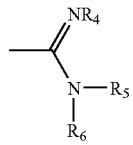 and 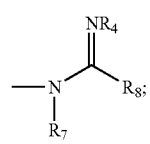

wherein:
$R_4$, $R_5$, $R_6$, $R_7$, and $R_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_5$ and $R_6$ together represent a $C_2$ to $C_{10}$ alkyl, hydroxyalkyl, or alkylene; or $R_8$ is

wherein:

$R_9$ and $R_{10}$ are each independently selected from the group consisting of H, alkyl, aryl, and $-OR_{11}$; and wherein:

$R_{11}$ is selected from the group consisting of H, alkyl, and aryl;

or a pharmaceutically acceptable salt thereof.

In some embodiments of the method of treating a microbial infection by administering to a subject in need of treatment thereof a compound of Formula I, X is $CH_2$ and Y is absent. In such embodiments, the fused-ring structure comprises 9H-fluorene. In some embodiments, A and A' are each independently

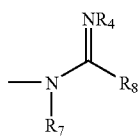

wherein:

p and q are each 1;

$R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and $R_8$ is selected from the group consisting of aryl and

wherein:

$R_9$ and $R_{10}$ are each independently selected from the group consisting of H, alkyl, aryl, and $-OR_{11}$;

wherein:

$R_{11}$, is selected from the group consisting of H, alkyl, and aryl.

In some embodiments, A and A' are in the 2- and 7-positions of the 9H-fluorene ring.

In some embodiments, m and n are both zero and $R_7$ is H. In some embodiments, $R_4$ is H and $R_8$ is phenyl. In some embodiments, $R_4$ is H and $R_8$ is 2-pyridyl.

In some embodiments, $R_8$ is

wherein:

$R_9$ and $R_{10}$ are each independently selected from the group consisting of H, alkyl, aryl, and $-OR_{11}$; and wherein:

$R_{11}$ is selected from the group consisting of H, alkyl, and aryl.

In some embodiments, $R_4$ and $R_9$ are each H. In some embodiments, $R_4$ is ethoxycarbonyl and $R_9$ is H. In some embodiments, $R_{10}$ is H. In some embodiments, $R_{10}$ is methyl. In some embodiments, $R_{10}$ is isopropyl. In some embodiments, $R_{10}$ is methoxyl. In some embodiments, $R_{10}$ is isobutoxyl.

In some embodiments of the method of treating a microbial infection by administering to a subject in need of treatment thereof a compound of Formula I, X is C=O and Y is absent. In such embodiments, the fused-ring structure comprises 9H-fluoren-9-one. In some embodiments, A and A' are each independently

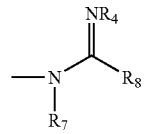

wherein:

p and q are each 1;

$R_4$ and $R_7$ are each independently selected from the group consisting of H alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and $R_8$ is selected from the group consisting of aryl and

wherein:

$R_9$ and $R_{10}$ are each independently selected from the group consisting of H, alkyl, aryl, and $-OR_{11}$; and wherein:

$R_{11}$ is selected from the group consisting of H, alkyl, and aryl.

In some embodiments, A and A' are in the 2- and 7-positions of the 9H-fluoren-9-one ring. In some embodiments, m and n are both zero and $R_7$ is H. In some embodiments, $R_8$ is

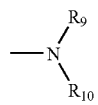

wherein:
  $R_9$ and $R_{10}$ are each independently selected from the group consisting of H, alkyl, aryl, and —$OR_{11}$;
  wherein:
    $R_{11}$ is selected from the group consisting of H, alkyl, and aryl.

In some embodiments, $R_9$ and $R_{10}$ are both H. In some embodiments, $R_4$ is H. In some embodiments, $R_4$ is ethoxycarbonyl.

In some embodiments of the method of treating a microbial infection by administering to a subject in need of treatment thereof a compound of Formula I, X and Y are both C=O. In such embodiments, the fused-ring structure comprises 9,10-anthraquinone. In some embodiments, A and A' are each independently

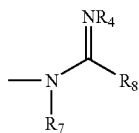

wherein:
  p and q are each 1;
  $R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
  $R_8$ is selected from the group consisting of aryl and

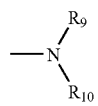

wherein:
  $R_9$ and $R_{10}$ are each independently selected from the group consisting of H, alkyl, aryl, and —$OR_{11}$;
  wherein:
    $R_{11}$ is selected from the group consisting of H, alkyl, and aryl.

In some embodiments, m and n are both zero and $R_7$ is H. In some embodiments, $R_8$ is

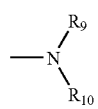

wherein:
  $R_9$ and $R_{10}$ are each independently selected from the group consisting of H, alkyl, aryl, and —$OR_{11}$;
  wherein:
    $R_{11}$ is selected from the group consisting of H, alkyl, and aryl.

In some embodiments, $R_9$ and $R_{10}$ are both H. In some embodiments, $R_4$ is H.

In some embodiments of the method of treating a microbial infection by administering to a subject in need of treatment thereof a compound of Formula I, X is N and Y is CH. In such embodiments, the fused-ring structure comprises acridine. In some embodiments, A and A' are each independently

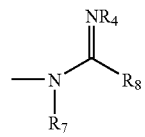

wherein:
  p and q are each 1;
  $R_4$ and $R_7$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
  $R_8$ is selected from the group consisting of aryl and

wherein:
  $R_9$ and $R_{10}$ are each independently selected from the group consisting of H, alkyl, aryl, and —$OR_{11}$; and
  wherein:
    $R_{11}$ is selected from the group consisting of H, alkyl, and aryl.

In some embodiments, A and A' are in the 3- and 6-positions of the acridine ring. In some embodiments, m and n are both zero and $R_7$ is H. In some embodiments, $R_8$ is

wherein:
  $R_9$ and $R_{10}$ are each independently selected from the group consisting of H, alkyl, aryl, and —$OR_{11}$; and
  wherein:
    $R_{11}$ is selected from the group consisting of H, alkyl, and aryl.

In some embodiments, $R_9$ and $R_{10}$ are both H. In some embodiments, $R_4$ is H.

In some embodiments of the method of treating a microbial infection by administering to a subject in need of treatment thereof a compound of Formula I, the method comprises a compound of Formula I selected from the group consisting of: 2,7-bis-guanidino-9H-fluorene; 2,7-bis-guanidinofluoren-9-one; 2,7-bis-guanidinoanthraquinone; 3,6-bis-guanidinoacridine; 2,7-bis-(N"-ethoxycarbonyl)guanidino-9H-fluorene; 2,7-bis(N''-ethoxycarbonyl)guanidinofluoren-9-one; 2,7-bis(N''-ethoxycarbonyl-N'-methyl)guanidino-9H-fluorene; 2,7-bis(N''-ethoxycarbonyl-N'-isopropyl)guanidino-9H-fluorene; 2,7-bis(N'-ethoxycarbonyl-N'-methoxy)guanidino-9H-fluorene; 2,7-bis(N''-ethoxycarbonyl-N'-isobutoxy) guanidine-9H-fluorene; 2,7-bis(N'-methyl)guanidino-9H-fluorene; 2,7-bis(N'-iso-propyl)guanidino-9H-fluorene; 2,7-bis(N'-methoxy)guanidino-9H-fluorene; 2,7-bis(N'-isobutoxy)guanidine-9H-fluorene; 2,7-bis[(phenylimino)amino)]-9H-fluorene; and 2,7-bis[(2-pyridylimino)amino)-9H-fluorene.

In some embodiments, the compound of Formula I is administered in the form of a pharmaceutically acceptable salt. In some embodiments, the pharmaceutically acceptable salt is a hydrochloride salt.

In some embodiments, the microbial infection is selected from one of a *Trypanosoma brucei rhodesiense* infection and a *Plasmodium falciparum* infection.

The subject treated in the presently disclosed subject matter in its many embodiments is desirably a human subject, although it is to be understood the methods described herein are effective with respect to all vertebrate species, which are intended to be included in the term "subject". The methods described herein are particularly useful in the treatment and/or prevention of infectious diseases in warm-blooded vertebrates. Thus, the methods can be used as treatment for mammals and birds.

More particularly, provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

EXAMPLES

The following Examples have been included to illustrate modes of the presently disclosed subject matter. Certain aspects of the following Examples are described in terms of techniques and procedures found or contemplated to work well in the practice of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Methods and Materials For Examples 1-4

Melting points were recorded using a Thomas-Hoover (Uni-Melt® (Thomas Scientific, Swedesboro, N.J., United States of America)) capillary melting point apparatus and are uncorrected. TLC analysis was carried out on silica gel 60 $F_{254}$ precoated aluminum sheets and detected under UV light. $^1$H and $^{13}$C—NMR spectra were recorded employing a Varian GX400 or Varian Unity Plus 300 spectrometer (Varian, Inc., Palo Alto, Calif., United States of America), and chemical shifts (δ) are in ppm relative to TMS as internal standard. Mass spectra were recorded on a VG Analytical 70-SE spectrometer (VG Analytical, Ltd., Manchester, United Kingdom). Elemental analyses were obtained from Atlantic Microlab Inc. (Norcross, Ga., United States of America) and are within ±0.4 of the theoretical values. The compounds reported as salts frequently analyzed correctly for fractional moles by water and/or ethanol of solivation. In each case $^1$H-NMR showed the presence of the indicated solvent(s). All chemicals and solvents (including anhydrous solvents) were purchased from Aldrich Chemical Co. (Milwaukee, Wis., United States of America), Fisher Scientific (Fairlawn, N.J., United States of America) or Frontier Scientific (Logan, Utah, United States of America) and used as purchased. Acetonitrile ($CaH_2$) and triethylamine ($CaH_2$) were distilled from the indicated drying agent. Synthesis of the bis-aminofluorenone (3b) and bis-aminoanthraquinone (3c) was achieved as described in Scheme 1 according to the literature. S-(2-naphthylmethyl) thioacetimidate was prepared adopting the reported procedure.

Example 1

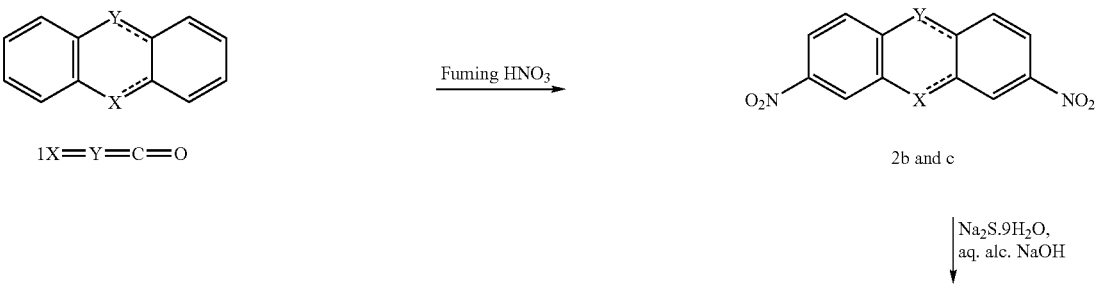

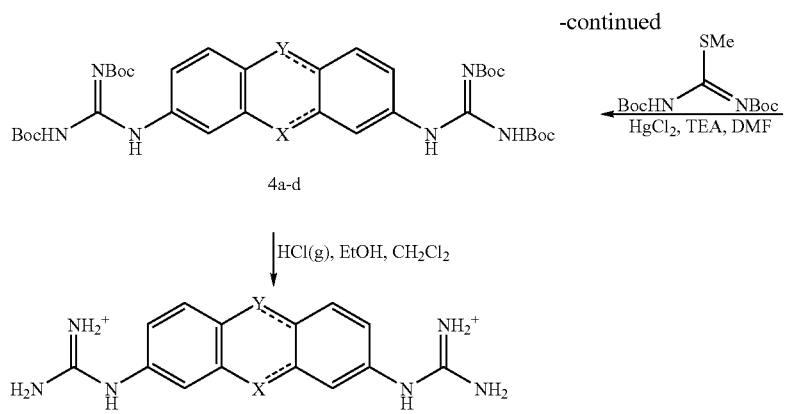
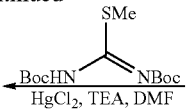
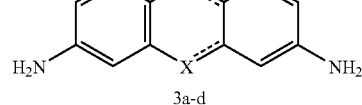

5a-d

Legend for compounds 2-5
a X = CH$_2$ Y = nil
b X = C═O Y = nil
c X = Y = C═O
d X = N Y = CH

Preparation of Bis(N',N''-di-BOCguanidino) Derivatives (General Procedure) (Scheme 1)

2,7-Bis(N',N''-di-BOCguanidino)-9H-fluorene (4a). To a solution of 2,7-diamino fluorene (3a) (0.49 g, 2.5 mmol) in anhydrous DMF (15 mL) was added 1,3-bis(tert-butoxycarbonyl)-2-methylthiopseudourea (1.56 g, 5.3 mmol), triethylamine (3.23 g, 32 mmol) and finally mercury(II)chloride (1.57 g, 5.7 mmol). The suspension was kept stirring at room temperature for 24 h. The reaction, diluted with CH$_2$Cl$_2$ and Na$_2$CO$_3$ solution, was filtered through a pad of Celite. The organic layer was washed with water (3×) followed by brine and then dried over anhydrous Na$_2$SO$_4$. After evaporating the solvent to dryness the obtained residue was recrystallized from CH$_2$Cl$_2$/MeOH giving a light yellow solid (1.15 g, 68%), mp>340° C. $^1$H-NMR (CDCl$_3$): δ 1.52,1.54 (2s, 36H), 3.91 (s, 2H), 7.47 (d, J=8.4 Hz, 2H), 7.64 (d, J=8.4 Hz, 2H), 7.90 (s, 2H), 10.43 (s, 2H), 11.68 (s, 2H). $^{13}$C-NMR (CDCl$_3$): δ 163.6, 153.5, 153.3, 144.2, 138.0, 135.2, 120.9, 119.7, 118.9, 83.6, 79.6, 37.2, 28.1, 28.1. Anal. Calcd. for C$_{35}$H$_{48}$N$_6$O$_8$ (680.79): C % 61.75, H % 7.11, N % 12.34. Found: C % 61.50, H %7.11, N % 12.36.

2,7-Bis(N',N''-di-BOCguanidino)fluoren-9-one (4b). Orange solid (1.16 g, 65%), mp>340° C. $^1$H-NMR (CDCl$_3$): δ 1.51,1.54 (2s, 36H), 7.42 (d, J=8.4 Hz), 7.77 (s, 2H), 7.82 (d, J=8.4 Hz, 2H), 10.46 (br s, 2H), 11.63 (br s, 2H). $^{13}$C-NMR (CDCl$_3$): δ 192.7, 163.3, 153.4, 153.2, 140.3, 137.4, 135.1, 128.0, 120.5, 118.5, 84.0, 79.9, 28.1, 28.0. Anal. Calcd. for C$_{35}$H$_{46}$N$_6$O$_9$-0.5H$_2$O (703.78): C % 59.73, H % 6.73, N % 11.94. Found: C % 59.69, H % 6.76, N % 12.13.

2,7-Bis(N',N''-di-BOCguanidino)anthraquinone (4c). Yellow solid (1.24 g, 82%), mp>340° C. $^1$H-NMR (CDCl$_3$): δ 1.56 (s, 36H), 8.24 (s, 2H), 8.30 (d, J=8.7 Hz, 2H), 8.43 (d, J=8.7 Hz, 2H), 10.82 (br s, 2H), 11.62 (br s, 2H). $^{13}$C-NMR (CDCl$_3$): δ 182.5, 181.2, 163.1, 153.2, 142.3, 134.4, 129.4, 128.9, 126.7, 119.0, 84.4, 80.3, 28.1, 28.0. Anal. Calcd. for C$_{36}$H$_{46}$N$_6$O$_{10}$-0.5CH$_2$Cl$_2$ (765.25): C % 57.28, H % 6.19. Found: C % 57.30, H % 6.09.

3,6-Bis(N',N''-di-BOCguanidino)acridine (4d). Canary yellow fluffy solid (0.88 g, 73%), mp>340° C. $^1$H-NMR (CDCl$_3$): δ 1.53, 1.55 (2s, 36H), 7.78 (dd, J=2.1 Hz, J=9.0 Hz, 2H), 7.9 (d, J=9.0 Hz, 2H), 8.45 (d, J=2.1 Hz, 2H), 8.6 (s, 1H), 10.69 (s, 2H), 11.68 (s, 2H). Anal. Calcd. for C$_{35}$H$_{47}$N$_7$O$_8$-0.5H$_2$O (702.79): C % 59.81, H % 6.88, N % 13.95. Found: C % 59.97, H % 6.88, N % 13.90.

Deprotection of N',N''-Di-BOCguanidines (General Procedure) (Scheme 1)

2,7-Bis-guanidino-9H-fluorene Dihydrochloride (5a). The N',N''-di-BOC-guanidine (4a) (0.25 g, 0.4 mmol) was dissolved in CH$_2$Cl$_2$ (10 mL), diluted with dry EtOH (15 mL) and the chilled solution was saturated with dry HCl. The reaction was then kept stirring at room temperature for 3 days (drying tube), when by the product started forming a precipitate over time. After evaporating the solvent to dryness, the residue was washed with ether multiple times and was dried under vacuum at 50-60° C. over night to give whitish yellow solid of the bis-guanidine dihydrochloride (0.13 g, quantitative), mp>340° C. $^1$H-NMR (DMSO-d$_6$): δ 3.95 (s, 2H), 7.24 (d, J=8.4 Hz, 2H), 7.45 (s, 2H), 7.58 (br s, 8H), 7.95 (d, J=8.4 Hz, 2H), 10.23 (br s, 2H). $^{13}$C-NMR (DMSO-d$_6$): δ 156.1, 156.1, 144.5, 138.6, 133.8, 123.3, 121.4, 120.9, 36.8. MS (EI): m/z 277 (M$^+$+1) (14), 252 (100). Anal. Calcd. for C$_{15}$H$_{16}$N$_6$.2HCl-0.25C$_2$H$_5$OH (364.76): C % 51.04, H % 5.39, N % 23.04, Cl % 19.44. Found: C % 50.74, H % 5.26, N % 22.99, Cl % 19.87.

2,7-Bis-guanidinofluoren-9-one Dihydrochloride (5b). Green solid (0.26 g, 89%), mp>340° C. $^1$H-NMR (DMSO-d$_6$): δ 7.45 (m, 4H), 7.68 (br s, 8H), 7.86 (d, J=8.4 Hz, 2H), 10.25 (br s, 2H). $^{13}$C-NMR (DMSO-d$_6$): δ 191.58, 159.03, 140.88, 136.54, 134.62, 130.77, 122.36, 119.86. MS (EI): m/z 295(M$^+$+1) (23), 278 (100). Anal. Calcd. for C$_{15}$H$_{14}$N$_6$O-2HCl-0.35H$_2$O (373.53): C % 48.23, H % 4.51, N % 22.49, Cl % 18.95. Found: C % 48.51, H % 4.55, N % 22.13, Cl % 18.93.

2,7-Bis-guanidinoanthraquinone Dihydrochloride (5c). Orange red solid (0.22 g, 91%), mp>340° C. dec. $^1$H-NMR (DMSO-d$_6$): δ 7.75 (d, J=8.4 Hz, 2H), 7.97 (s, 2H), 8.06 (br s, 8H), 8.24 (d, J=8.4 Hz, 2H), 10.87 (br s, 2H). $^{13}$C-NMR (DMSO-d$_6$): δ 181.5, 180.4, 155.5, 142.0, 134.1, 129.2, 128.9, 127.6, 119.3. MS (EI): m/z 290 (M$^+$) (3). Anal. Calcd.

for C$_{16}$H$_{14}$N$_6$O$_2$·2HCl·1.66H$_2$O (425.15): C % 45.20, H % 4.58, N % 19.77. Found: C % 45.24, H % 4.58, N % 19.47.

3,6-bis-guanidinoacridine Trihydrochloride (5d). Orange solid (0.33 g, 85%), mp>340° C. $^1$H-NMR (DMSO-d$_6$): δ 7.75 (dd, J=8.4 Hz, 2H), 7.96 (d, J=2.1 Hz, 2H), 8.06 (br s, 8H), 8.23 (d, J=8.4 Hz, 2H), 10.83 (br s, 2H). $^{13}$C-NMR (DMSO-d6): δ 181.5, 180.4, 155.5, 142.0, 134.1, 129.2, 128.9, 127.6, 119.3. Anal. Calcd. for C$_{15}$H$_{15}$N$_7$·3HCl·C$_2$H$_5$OH·0.33H$_2$O (454.72): C % 44.90, H % 4.46, N % 21.56. Found: C % 45.08, H % 5.10, N % 21.48.

Example 2

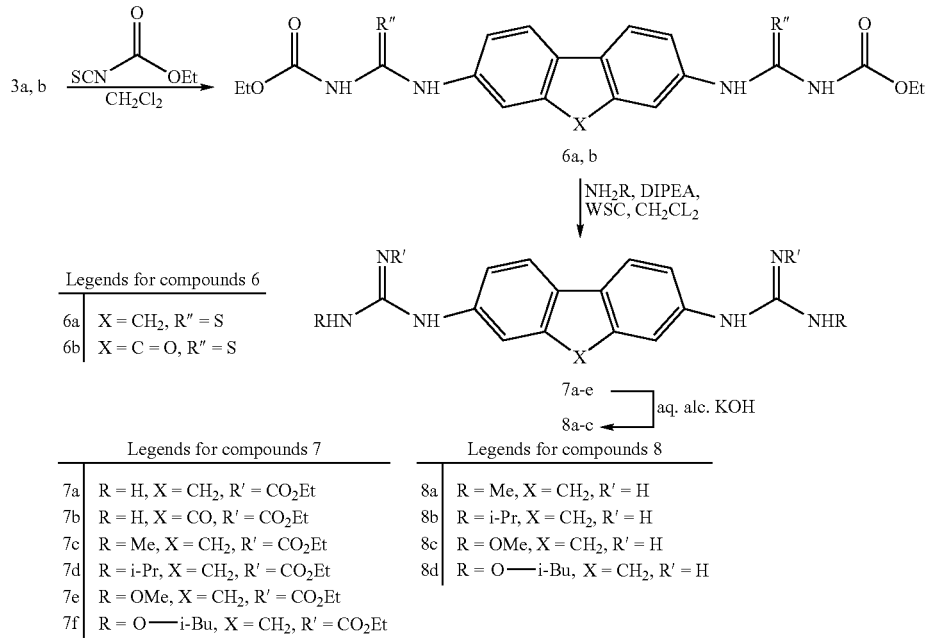

Preparation of Carbamoyl Thiourea Derivatives (Scheme 2)

2,7-Bis(N''-ethoxycarbonylthiourea)-9H-fluorene (6a). A solution of 2,7-diamino-9H-fluorene (3a) (1g, 5.1 mmol) in CH$_2$Cl$_2$ (10 mL), added to which ethyl isothiocyanatoformate (1.47 g, 11.2 mmol), was stirred at room temperature for 24 h. After flash chromatography, the reaction was diluted with hexane and the precipitate formed was collected and dried to yield the bis-carbamoylthiourea as a light brown solid (2.32 g, quantitative), mp>340° C. dec. $^1$H-NMR (DMSO-d$_6$): δ 1.27 (t, J=6.9 Hz, 6H), 3.95 (s, 2H), 4.23 (q, J=6.9 Hz, 4H), 7.75 (d, J=8.4 Hz, 2H), 7.89 (m, 4H), 11.28 (s, 2H), 11.64 (s, 2H). $^{13}$C-NMR(DMSO-d$_6$): δ 163.2, 158.9, 143.6, 137.9, 135.8, 123.1, 121.1, 119.8, 59.5, 36.4, 28.0, 14.5. MS (EI): m/z 459 (M$^+$+1, 18), 374.1 (8), 328 (100), 319 (8), 151 (12).

2,7-Bis(N''-ethoxycarbonylthiourea)fluoren-9-one (6b). To a suspension of 2,7-diaminofluorenone (3b) (0.3g, 1.4 mmol) in toluene (10 mL), was added 0.41 g (3.1 mmol) ethyl isothiocyanatoformate. The reaction mixture was refluxed for 10 h. After cooling to room temperature, the reaction was diluted with hexane. The orange precipitate obtained was filtered off, washed with hexane and dried under vacuum (0.66 g, 98%), mp>340° C. dec. $^1$H-NMR (DMSO-d$_6$): δ 1.26 (t, J=7.2 Hz, 6H), 4.22 (q, J=7.2 Hz, 4H), 7.69 (dd, J=1.8, 8.1 Hz, 2H), 7.80 (d, J=8.1 Hz, 2H), 7.97 (d, J=1.8 Hz, 2H), 11.39 (s, 2H), 11.60 (s, 2H).

Preparation of N-Substituted Carbamoyl Guanidines (General Procedure) (Scheme 2)

2,7-Bis(N''-ethoxycarbonyl)guanidino-9H-fluorene (7a). A stirred solution of carbamoyl thiourea (6a) (0.58 g, 1.2 mmol), ammonia (0.5M solution in dioxane) (10 mL, 5.0 mmol), and diisopropylethylamine (0.98 g, 7.5 mmol) in anhydrous CH$_2$Cl$_2$ (10 mL) was cooled to 0° C. EDCI (0.96 g, 5.0 mmol) was added, and the solution was stirred at room temperature over night. The reaction mixture was washed with water (3×), followed by brine and dried over anhydrous Na$_2$SO$_4$. The residue remaining after removal of the solvent was crystallized from EtOH/water (0.45 g, 84%), mp>340° C. $^1$H-NMR (DMSO-d$_6$): δ 1.16 (t, J=7.2 Hz, 6H), 3.87(s, 2H), 3.98 (q, J=7.2 Hz, 4H), 7.33 (d, J=8.4 Hz, 2H), 7.65 (s, 2H), 7.75 (d, J=8.4 Hz, 2H), 9.31 (br s, 2H). $^{13}$C-NMR (DMSO-d$_6$): δ 163.1, 159.0, 143.4, 136.8, 136.3, 120.4, 119.3, 118.3, 59.4, 36.4, 14.4. Anal. Calcd. for C$_{21}$H$_{24}$N$_6$O$_4$·0.5C$_2$H$_5$OH (447.48): C % 59.04, H % 6.08, N % 18.78. Found: C % 58.96, H % 5.74, N % 18.88.

2,7-Bis(N''-ethoxycarbonyl)guanidinofluoren-9-one (7b). Brick red solid (0.35 g, 75%), mp>340° C. $^1$H-NMR (DMSO-d$_6$): δ 1.17 (t, J=7.0 Hz, 6H), 4.00 (q, J=7.0 Hz, 4H), 7.47 (dd, J=1.8, 8.1 Hz, 2H), 7.59 (d, J=8.1 Hz, 2H), 7.77 (d, J=1.8 Hz, 2H), 9.31 (br s, 2H). $^{13}$C-NMR (DMSO-d$_6$): δ 192.9, 162.5, 158.6, 139.6, 138.3, 134.1, 126.4, 120.8, 116.6, 59.8, 14.5. Anal. Calcd. for C$_{21}$H$_{24}$N$_6$O$_5$·0.15CH$_2$Cl$_2$ (451.17): C % 56.54, H % 5.08, N % 18.47. Found: C % 56.30, H % 4.98, N % 18.62.

2,7-Bis(N''-ethoxycarbonyl-N'-methyl)guanidino-9H-fluorene (7c). Adopting the same procedure followed for preparation of (7a), methylamine (2M solution in THF) was used for transformation of the thiourea compound into N-substituted guanidine. The reaction yielded an off-white solid (0.53 g, 93%), mp 157-8° C. $^1$H-NMR (DMSO-d$_6$): δ 1.15 (t, J=7.2 Hz, 6H), 2.83 (s, 6H), 3.90 (s, 2H), 3.94 (q, J=7.2 Hz, 4H), 7.32 (d, J=8.4 Hz, 2H), 7.54 (s, 2H), 7.83 (d, J=8.4 Hz, 2H). $^{13}$C-NMR (DMSO-d$_6$): δ 161.9, 157.9, 143.7, 137.6, 135.9, 123.1, 121.0, 119.9, 59.9, 36.4, 28.3, 14.5. MS (FAB, thioglycerol): m/z 453 (M$^+$+1, 100), 407 (39), 323 (15). Anal. Calcd. for C$_{23}$H$_{28}$N$_6$O$_4$—H$_2$O (470.52): C % 58.71, H % 6.42, N % 17.86. Found: C % 58.81, H % 6.39, N % 17.71.

2,7-Bis(N''-ethoxycarbonyl-N'-iso-propyl)guanidino-9H-fluorene (7d). Using iso-propylamine and carrying out the same synthetic steps used for (7a), a beige solid was obtained (0.39 g, 88%), mp 1424° C. $^1$H-NMR (DMSO-d$_6$): δ 0.84 (t, J=7.2 Hz, 6H), 1.17 (m, 12H), 3.88 (s, 2H), 3.93 (q, J=7.2 Hz, 4H), 4.11 (m, 2H), 7.31 (d, J=8.4 Hz, 2H), 7.52 (s, 2H), 7.80 (d, J=8.4 Hz, 2H). $^{13}$C-NMR (DMSO-d$_6$): δ 163.4, 157.3, 143.5, 137.3, 136.2, 122.9, 120.9, 119.7, 59.6, 42.3, 36.4, 22.5, 14.5. MS (ES): m/z 509 (M$^+$+1) (19), 255 (100). Anal. Calcd. for C$_{27}$H$_{36}$N$_6$O$_4$-0.25 C$_2$H$_5$OH (520.13): C % 63.50, H % 7.26, N % 16.15. Found: C % 63.20, H % 7.06, N % 16.35.

2,7-Bis(N''-ethoxycarbonyl-N'-methoxy)guanidino-9H-fluorene (7e). Adopting the general procedure and using methylhydoxylamine, a tan white solid was obtained (0.55 g, 87%), mp 180-2° C. $^1$H-NMR (DMSO-d$_6$): δ 1.20 (t, J=7.2 Hz, 6H), 3.68 (s, 6H), 3.76 (s, 2H), 4.10 (q, J=7.2 Hz, 4H), 6.99 (d, J=8.1 Hz, 2H), 7.16 (s, 2H), 7.35 (dd, J=1.8, 8.1 Hz, 2H), 8.35 (s, 2H), 8.70 (s, 2H).

2,7-Bis(N''-ethoxycarbonyl-N'-isobutoxy)guanidino-9H-fluorene (7f). Following the general procedure, O-isobutyl-hydroxylamine was used to prepare the target compound, which was obtained as creamy white crystals (0.8 g, 93%), 122-5° C.; $^1$H-NMR (DMSO-d$_6$) 60.88-0.99 (m, 30H), 1.21 (t, J=7.2 Hz, 6H), 1.92-2.02 (m, 4H), 3.65 (d, J=6.6 Hz, 8H), 3.74-3.78 (m, 4H), 3.85 (q, J=7.2 Hz, 4H), 4.11 (q, J=7.2 Hz, 4H), 7.00 (d, J=8.1 Hz, 2H), 7.17 (s, 2H), 7.35 (d, J=8.1 Hz, 2H), 7.55-7.62 (m, 6H), 8.19 (br s, 1H), 8.21 (br s, 1H), 8.67 (br s, 1H), 8.68 (br s, 1H), 9.01 (br s, 1H), 9.02 (br s, 1H), 9.10 (br s, 1H), 9.11 (br s, 1H); $^{13}$C-NMR (DMSO-d$_6$) δ 154.0, 153.9, 153.3, 143.4, 143.3, 143.1, 142.9, 142.9, 142.3, 142.2, 138.8, 138.6, 137.9, 137.7, 135.8, 135.6, 134.4, 134.2, 119.7, 119.4, 199.1, 118.8, 117.7, 117.6, 116.6, 114.5,79.5, 79.3, 61.1, 60.4, 36.6, 36.5, 36.3, 27.3, 27.3, 19.3, 14.4; MS (ESI) m/z (rel. int.) 569 (M$^+$+1, 100). Anal. Calcd. for C$_{29}$H$_{40}$N$_6$O$_6$ (568.66): C % 61.25, H % 7.08. Found: C % 61.12, H % 7.29.

Preparation of N-Substituted Guanidines (General Procedure) (Scheme 2)

2,7-Bis(N'-methyl)guanidino-9H-fluorene (8a). The substituted guanidine (7c) (0.5 g, 1.1 mmol) was suspended in EtOH (5 mL). 1 N KOH (11 mL, 11 mmol) was then added and the reaction mixture was kept stirring over night maintaining the temperature at 55-60° C. The solvent was evaporated to dryness, the residue was washed multiple times with water and recrystallized from aqueous EtOH to give a light orange solid (0.24 g, 70%), mp 240-2° C. dec. $^1$H-NMR (DMSO-d$_6$): δ 2.6 (s, 6H), 3.69 (s, 2H), 6.70 (d, J=2.7 Hz, 2H), 6.90 (s, 2H), 7.50 (d, J=2.7 Hz, 2H). For preparing the HCl salt, the free base was dissolved in dry EtOH (20 mL) and the solution was chilled in an ice-bath. After passing HCl gas for 10 min, the reaction was concentrated under reduced pressure and then diluted with ether. The precipitate formed was collected by filtration to give an orange solid (0.16 g, 65%), mp 276-8° C. $^1$H-NMR (DMSO-d$_6$): δ 2.84 (s, 6H), 3.96 (s, 2H), 7.25 (d, J=8.4 Hz, 2H), 7.46 (s, 2H), 7.77 (br s, 2H), 7.89 (br s, 2H), 7.95 (d, J=8.4 Hz, 2H), 10.01 (br s, 2H). $^{13}$C-NMR (DMSO-d$_6$): δ 155.6, 144.5, 138.5, 134.1, 123.5, 121.5, 120.9, 36.5, 28.3. MS (ES): m/z 309 (M$^+$+1) (100), 155 (9). Anal. Calcd. for C$_{17}$H$_{20}$N$_6$.2HCl-0.25C$_2$H$_5$OH-0.75H$_2$O (406.33): C % 51.73, H % 6.20, N % 20.68. Found: C % 51.77, H % 6.24, N % 20.48.

2,7-Bis(N-iso-propyl)guanidino-9H-fluorene (8b). Free base: Starting with 7d and following the general procedure, a salmon orange solid (0.17 g, 79%), mp 247-9° C. dec. $^1$H-NMR (DMSO-d$_6$): δ 1.11 (d, J=5.4 Hz, 12H), 3.68 (s, 2H), 3.85 (m, 2H), 4.93 (br s, 4H), 5.38 (br s, 2H), 6.69 (d, J=8.1 Hz, 2H), 6.89 (s, 2H), 7.49 (d, J=8.1 Hz, 2H). Dihydrochloride salt: Shiny yellow crystals, mp 308-9° C. dec. $^1$H-NMR (DMSO-d$_6$): δ 1.18 (d, J=6.3 Hz, 12H), 3.94 (m, 4H), 7.23 (d, J=8.4 Hz, 2H), 7.43 (s, 2H), 7.71 (br s, 4H), 7.93 (d, J=8.4 Hz, 2H), 8.06 (br s, 2H), 9.88 (br s, 2H). $^{13}$C-NMR (DMSO-d$_6$): δ 153.9, 144.8, 138.8, 134.5, 123.6, 121.6, 121.0, 43.8, 22.2. Anal. Calcd. for C$_{21}$H$_{28}$N$_6$-2HCl-1.5H$_2$O (464.54): C % 54.31, H % 7.16, N % 18.09. Found: C % 54.51, H % 6.74, N % 17.79.

2,7-Bis(N'-methoxy)guanidino-9H-fluorene (8c). Free base: Using 7e as a starting material, a pink solid (0.17 g, 79%), mp 200-2° C. dec. $^1$H-NMR (DMSO-d$_6$): δ 3.34 (br s, 4H), 3.74 (s, 2H), 5.29 (s, 6H), 7.20 (dd, J=1.8, 8.1 Hz, 2H), 7.50 (m, 4H), 7.75 (br s, 2H). $^{13}$C-NMR (DMSO-d$_6$): δ 151.6, 143.0, 139.5, 133.6, 118.7, 116.1, 114.1, 60.5, 36.5. Dihydrochloride salt: Shiny tan white solid, mp 264-7° C. dec. $^1$H-NMR (DMSO-d$_6$): δ 1.18 (d, J=6.3 Hz, 12H), 3.94 (m, 4H), 7.23 (d, J=8.4 Hz, 2H), 7.43 (s, 2H), 7.71 (br s, 4H), 7.93 (d, J=8.4 Hz, 2H), 8.06 (br s, 2H), 9.88 (br s, 2H). $^{13}$C-NMR (DMSO-d$_6$): δ 153.9, 144.8, 138.8, 134.5, 123.6, 121.6, 121.0, 43.8, 22.2. Anal. Calcd. for C$_{17}$H$_{20}$N$_6$O$_2$.2HCl-0.6H$_2$O (424.11): C % 48.14, H % 5.51, N % 19.80. Found: C % 48.35, H % 5.38, N % 19.41.

2,7-Bis(N'-isobutoxy)guanidino-9H-fluorene (8d). Free base: Starting with 7f and using the general procedure provided a brick red solid (0.16 g, 62%), mp 198-200° C.; $^1$H-NMR (DMSO-d$_6$) δ 0.90 (d, J=6.9 Hz, 12H), 1.93-2.02 (m, 2H), 3.55 (d, J=6.9 Hz, 4H), 3.74 (s, 2H), 5.32 (br s, 4H), 7.21 (dd, J=8.4, 1.8 Hz, 2H), 7.49-7.52 (m, 4H), 7.82 (br s, 2H); $^{13}$C-NMR (DMSO-d$_6$) δ 151.5, 143.1, 139.4, 133.8, 118.8, 116.3, 114.3, 79.1, 36.5, 27.3, 19.3; MS (ESI) m/z (rel. int.) 425 (M$^+$+1, 100), 245 (10), 156 (56); MS (ESI) m/z (rel. int.) 425 (M$^+$+1, 100), 254 (10), 156 (55). Hydrochloride salt: Pink solid, mp 251-2° C. (dec.); $^1$H-NMR (DMSO-d$_6$) δ 0.91 (d, J=6.9 Hz, 12H), 1.97-2.06 (m, 2H), 3.65 (d, J=6.9 Hz, 4H), 3.95 (s, 2H), 7.28 (d, J=8.4 Hz, 2H), 7.48 (s, 2H), 7.96 (d, J=8.4 Hz, 2H), 8.16 (br s, 4H), 10.36 (br s, 2H), 11.65 (br s, 2H). Anal. Calcd. for C$_{23}$H$_{32}$N$_6$O$_2$.2HCl (496.21): C % 55.53, H % 6.88, N % 16.89. Found: C % 55.45, H % 6.87, N % 16.70.

Example 3

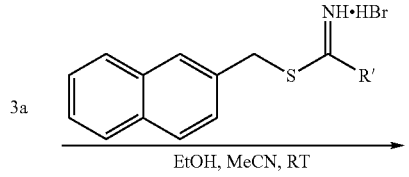

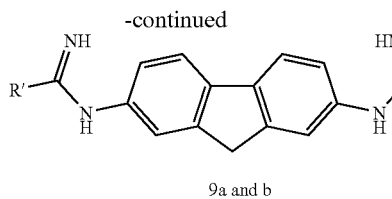

a R' = phenyl
b R' = 2-pyridyl 9a and b

Preparation of Reversed Amidines (General Procedure) (Scheme 3)

2,7-Bis[(phenylimino)amino]-9H-fluorene (9a). A solution of 2,7-diamino-9H-fluorene (0.3 g, 1.5 mmol) in dry MeCN (10 mL) was diluted with dry EtOH (15 mL) and chilled in an ice-water bath. The solution was then treated with S-(2-naphthymethyl)-thiobenzimidate hydrobromide (1.13 g, 3.2 mmol). Free base: The reaction was kept stirring at room-temperature for 24 h after which the solvent was evaporated to dryness leaving behind an oily residue that was triturated with ether to give a solid of the hydrobromide salt. The solid was then dissolved in EtOH, basified with 1 N NaOH and the free base extracted with EtOAc. After drying over $Na_2SO_4$, the solvent was evaporated to dryness, giving an off white solid (0.45 g, 63%), mp 240-2° C. $^1$H-NMR (DMSO-$d_6$): δ 3.83 (s, 2H), 6.31 (br s, 4H), 6.83 (m, 2H), 7.04 (s, 2H), 7.45 (d, J=7.2 Hz, 6H), 7.71 (d, J=8.1 Hz, 2H), 7.97 (d, J=7.8 Hz, 4H). $^{13}$C-NMR (DMSO-$d_6$): δ 153.9, 148.4, 143.7, 135.9, 135.7, 129.9, 127.9, 126.9, 120.2, 119.6, 118.3, 36.4. Hydrochloride salt: An ice-bath cold solution of the free base in Dry EtOH was treated with HCl gas for 5-10 min, after which the solvent was concentrated to near dryness and the suspension was diluted with ether to furnish a yellow solid (0.28 g), mp 286-8° C. $^1$H-NMR (DMSO-$d_6$): δ 4.05 (s, 2H), 7.53 (d, J=8.4 Hz, 2H), 7.68 (m, 4H), 7.79 (m, 4H), 7.96 (m, 2H), 8.16 (d, J=8.4 Hz, 2H), 9.16 (br s, 2H), 9.86 (br s, 2H), 11.67 (br s, 2H). $^{13}$C-NMR: δ 163.0, 144.9, 140.1, 133.7, 133,6, 128.9, 128.6, 124.4, 122.4, 121.5, 36.95. MS (EI): m/z 402 (M+, 100), 299 (38), 197 (9), 196 (60), 151 (7), 103 (32), 77 (10). Anal. Calcd. for $C_{27}H_{22}N_4 \cdot 2HCl \cdot 0.25C_2H_5OH$—$H_2O$ (504.94): C % 65.41, H % 5.49, N % 11.09, Cl % 14.04. Found: C % 65.76, H % 5.40, N % 10.87, Cl % 14.09.

2,7-Bis[(2-pyridylimino)amino]-9H-fluorene (9b). Free base: Shiny yellow crystals (0.70 g, 67%), mp 230-2° C. $^1$H-NMR (DMSO-$d_6$): δ 4.74 (s, 2H), 6.56 (br s, 4H), 7.79 (d, J=8.4 Hz, 2H), 7.99 (s, 2H), 8.41 (t, J=7.8 Hz, 2H), 8.61 (d, J=8.4 Hz, 2H), 8.81 (t, J=7.8 Hz, 2H), 9.16 (d, J=7.8 Hz, 2H), 8.48 (d, J=7.8 Hz, 2H). Hydrochloride salt: Yellow solid (0.33 g), mp 3024° C. $^1$H-NMR (DMSO-$d_6$): δ 4.08 (s, 2H), 7.53 (d, J=8.1 Hz, 2H), 7.74 (s, 2H), 7.85, (t, J=7.5 Hz, 2H), 8.16 (d, J=7.5 Hz, 2H), 8.21 (t, J=7.5 Hz, 2H), 8.58 (d, J=7.5 Hz, 2H), 8.89 (d, J=7.5 Hz, 2H), 9.39 (br s, 2H), 10.18 (br s, 2H). $^{13}$C-NMR (DMSO-$d_6$): δ 159.6, 149.7, 144.0, 143.8, 140.4, 138.4, 133.5, 128.6, 124.9, 124.2, 122.9, 121.8. MS (EI): m/z 404 (M+, 100), 300 (28), 283 (6), 196 (33), 152 (9), 105 (28), 78(21). Anal. Calcd. for $C_{25}H_{20}N_6 \cdot 3.5HCl \cdot 0.33C_2H_5OH$—$H_2O$ (565.29): C % 54.52, H % 4.89, N % 14.87, Cl % 21.95. Found: C % 54.57, H % 4.74, N % 14.97, Cl % 21.87.

Preparation of Amidines (General Procedure)

The amidines are made by standard protocols starting with readily available dibromo analogs, which are converted into the corresponding bis-nitriles. The key intermediate bis-nitriles are converted into the amidines using the Pinner approach. For standard protocols for preparing amidines, see Das, B. P. et al., *J. Med. Chem.* 1977, 20, 531; Boykin. D. W. et al., *J. Med. Chem.* 1995, 38, 912; and Ismail, M. et al. *J. Med. Chem.*, 2003, 46, 4761-4769, which references are incorporated herein by reference.

Example 4

Table 1 shows potent in vitro data for certain compounds of Formula I. Two compounds (8a and 5b) show IC-50 values versus *Trypanosoma brucei rhodesiense* (T.b.r.) at 13 nM or less. Two compounds (5a and 8a) show IC-50 values versus *Plasmodium falciparum* (p.f.) at 10 nM or less. Compounds 8a and 8b give 3/4 and 4/4 cures versus the virulent STIP90° strain of T.b.r. in a mouse model. Prodrugs of these compounds hold promise as an oral treatment of both malaria and human African trypanosomiasis.

TABLE 1

Anti-protozoan Data for Fused Ring Dicationic Compounds.

| Compound | X | Y | R | R' | DNA ΔTm poly dA-dT | T.b.r. IC50 nM | P.f. IC50 NM | T.b.r. Cures | T.b.r. survival days |
|---|---|---|---|---|---|---|---|---|---|
| 5a | CH₂ | Nil | H | H | 13.6 | 24 | 2.3 | 0/4 | 6 |
| 5b | C=O | Nil | H | H | 6.1 | 7.3 | 268 | 2/4 | 50.75 |
| 5c | C=O | C=O | H | H | 7.2 | 128 | 23.5 | 0/4 | 27 |
| 5d | N | CH | H | H | 7.7 | 67 | 227 | 0/4 | 16.25 |
| 7a | CH₂ | Nil | H | CO₂Et | 0.3 | 1.4k | 2.1k | 0/4 | 18.75 |
| 7b | C=O | Nil | H | CO₂Et | −0.3 | 1.2K | 3.2K | 0/4 | 6 |
| 7c | CH₂ | Nil | Me | CO₂Et |  | 2.9k | 1.0k |  |  |
| 7d | CH₂ | Nil | i-Pr | CO₂Et | −0.5 | 2.5K | 6.3K | 0/4 | 17.75 |
| 8a | CH₂ | Nil | Me | H | 10.1 | 13 | 10 | 3/4 | 52 |

TABLE 1-continued

Anti-protozoan Data for Fused Ring Dicationic Compounds.

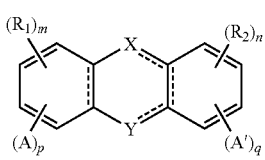

| Compound | X | Y | R | R' | DNA ΔTm poly dA-dT | T.b.r. IC50 nM | P.f. IC50 NM | In vivo T.b.r. Cures | T.b.r. survival days |
|---|---|---|---|---|---|---|---|---|---|
| 8b | CH$_2$ | Nil | i-Pr | H | 9.3 | 40.4 | 35.7 | 4/4 | 60 |
| 8c | CH$_2$ | Nil | OMe | H | | | | | |
| 8d | CH$_2$ | Nil | Oi-Bu | H | | | | | |
| 9a | CH$_2$ | Nil | a) | H | 22 | 292 | 481 | 0/4 | 7 |
| 9b | CH$_2$ | Nil | b) | H | 15.2 | 894 | 1.2k | | | nil = absent;
Me = methyl;
Et = ethyl;
i-Pr = isopropyl;
i-Bu = isobutyl;
OMe = methoxyl; and Oi-Bu = isobutoxyl;
a dashed line in the aromatic ring indicates that the bond is either present or absent.
a) = NHR replaced by phenyl;
b) = NHR replaced by 2-pyridyl.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A compound of Formula I:

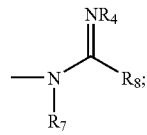

(I)

wherein:
X and Y are each independently selected from the group consisting of CH, CH$_2$, N, C=O, S, and NR$_3$,
wherein R$_3$ is selected from the group consisting of H, alkyl, aryl, alkoxyl, and aryloxyl, and
Y can be present or absent, and when absent, is replaced by a direct bond;
R$_1$ and R$_2$ are each independently selected from the group consisting of H, alkyl, halo, hydroxyl, alkoxyl, aryloxyl, and aralkyloxyl;
m and n are integers from 0 to 3, provided that when m is zero, R$_1$ is an implied hydrogen, and when n is zero, R$_2$ is an implied hydrogen;
p and q are each 1;
A and A' are each

wherein:
R$_4$, R$_7$, and R$_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
R$_8$ is

—N(R$_9$)(R$_{10}$)

wherein:
R$_9$ and R$_{10}$ are each independently selected from the group consisting of H, alkyl, aryl, and —OR$_{11}$;
wherein:
R$_{11}$ is selected from the group consisting of H, alkyl, and aryl.

2. The compound of claim 1, wherein:
X is CH$_2$; and
Y is absent.

3. The compound of claim 2, wherein $R_8$ is selected from the group consisting of aryl and

wherein:
  $R_9$ and $R_{10}$ are each independently selected from the group consisting of H, alkyl, aryl, and —$OR_{11}$;
  wherein:
    $R_{11}$ is selected from the group consisting of H, alkyl, and aryl.

4. The compound of claim 3, wherein:
m and n are both zero; and
$R_7$ is H.

5. The compound of claim 4, wherein:
$R_4$ is H; and
$R_8$ is phenyl.

6. The compound of claim 4, wherein:
$R_4$ is H; and
$R_8$ is 2-pyridyl.

7. The compound of claim 4, wherein $R_8$ is

wherein:
  $R_9$ and $R_{10}$ are each independently selected from the group consisting of H, alkyl, aryl, and —$OR_{11}$; and
  wherein:
    $R_{11}$ is selected from the group consisting of H, alkyl, and aryl.

8. The compound of claim 7, wherein $R_4$ and $R_9$ are each H.
9. The compound of claim 8, wherein $R_{10}$ is H.
10. The compound of claim 8, wherein $R_{10}$ is methyl.
11. The compound of claim 8, wherein $R_{10}$ is isopropyl.
12. The compound of claim 8, wherein $R_{10}$ is methoxyl.
13. The compound of claim 8, wherein $R_{10}$ is iso-butoxyl.
14. The compound of claim 7, wherein:
$R_4$ is ethoxycarbonyl; and
$R_9$ is H.
15. The compound of claim 14, wherein $R_{10}$ is H.
16. The compound of claim 14, wherein $R_{10}$ is methyl.
17. The compound of claim 14, wherein $R_{10}$ is isopropyl.
18. The compound of claim 14, wherein $R_{10}$ is methoxyl.
19. The compound of claim 14, wherein $R_{10}$ is iso-butoxyl.
20. The compound of claim 1, wherein:
X is C=O; and
Y is absent.
21. The compound of claim 20, wherein $R_8$ is selected from the group consisting of aryl and

wherein:
  $R_9$ and $R_{10}$ are each independently selected from the group consisting of H, alkyl, aryl, and —$OR_{11}$; and
  wherein:
    $R_{11}$ is selected from the group consisting of H, alkyl, and aryl.

22. The compound of claim 21, wherein:
m and n are both zero; and
$R_7$ is H.

23. The compound of claim 22, wherein $R_8$ is

wherein:
  $R_9$ and $R_{10}$ are each independently selected from the group consisting of H, alkyl, aryl, and —$OR_{11}$;
  wherein:
    $R_{11}$ is selected from the group consisting of H, alkyl, and aryl.

24. The compound of claim 23, wherein $R_9$ and $R_{10}$ are both H.
25. The compound of claim 24, wherein $R_4$ is H.
26. The compound of claim 24, wherein $R_4$ is ethoxycarbonyl.
27. The compound of claim 1 wherein:
X and Y are both C=O.
28. The compound of claim 27, wherein $R_8$ is selected from the group consisting of aryl and

wherein:
  $R_9$ and $R_{10}$ are each independently selected from the group consisting of H, alkyl, aryl, and —$OR_{11}$;
  wherein:
    $R_{11}$ is selected from the group consisting of H, alkyl, and aryl.

29. The compound of claim 28, wherein:
m and n are both zero; and
$R_7$ is H.
30. The compound of claim 29, wherein $R_8$ is

wherein:
  $R_9$ and $R_{10}$ are each independently selected from the group consisting of H, alkyl, aryl, and —$OR_{11}$;
  wherein:
    $R_{11}$ is selected from the group consisting of H, alkyl, and aryl.

31. The compound of claim 30, wherein $R_9$ and $R_{10}$ are both H.

32. The compound of claim 31, wherein $R_4$ is H.

33. The compound of claim 1, wherein:
X is N; and
Y is CH.

34. The compound of claim 33, wherein $R_8$ is selected from the group consisting of aryl and

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

35. The compound of claim 34, wherein:
m and n are both zero; and
$R_7$ is H.

36. The compound of claim 35, wherein $R_8$ is

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

37. The compound of claim 36, wherein $R_9$ and $R_{10}$ are both H.

38. The compound of claim 37, wherein $R_4$ is H.

39. The compound of claim 1, wherein the compound is selected from the group consisting of:
2,7-bis-guanidino-9H-fluorene;
2,7-bis-guanidinofluoren-9-one;
2,7-bis-guanidinoanthraquinone;
3,6-bis-guanidinoacridine;
2,7-bis-(N''-ethoxycarbonyl)guanidino-9H-fluorene;
2,7-bis(N''-ethoxycarbonyl)guanidinofluoren-9-one;
2,7-bis(N''-ethoxycarbonyl-N'-methyl)guanidino-9H-fluorene;
2,7-bis(N''-ethoxycarbonyl-N'-isopropyl)guanidino-9H-fluorene;
2,7-bis(N''-ethoxycarbonyl-N'-methoxy)guanidino-9H-fluorene;
2,7-bis(N''-ethoxycarbonyl-N'-isobutoxy)guanidine-9H-fluorene;
2,7-bis(N'-methyl)guanidino-9H-fluorene;
2,7-bis(N'-iso-propyl)guanidino-9H-fluorene;
2,7-bis(N'-methoxy)guanidino-9H-fluorene;
2,7-bis(N'-isobutoxy)guanidine-9H-fluorene;
2,7-bis[(phenylimino)amino)]-9H-fluorene; and
2,7-bis[(2-pyridylimino)amino)-9H-fluorene.

40. A pharmaceutically acceptable salt, wherein the pharmaceutically acceptable salt is the salt of a compound of Formula I:

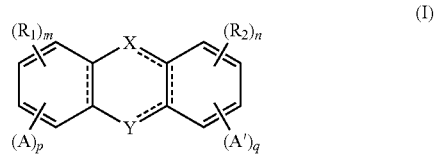

wherein:
X and Y are each independently selected from the group consisting of CH, $CH_2$, N, C=O, S, and $NR_3$,
wherein $R_3$ is selected from the group consisting of H, alkyl, aryl, alkoxyl, and aryloxyl, and
Y can be present or absent, and when absent, is replaced by a direct bond;
$R_1$ and $R_2$ are each independently selected from the group consisting of H, alkyl, halo, hydroxyl, alkoxyl, aryloxyl, and aralkyloxyl;
m and n are integers from 0 to 3, provided that when m is zero, $R_1$ is an implied hydrogen, and when n is zero, $R_2$ is an implied hydrogen;
p and q are each 1;
A and A' are each

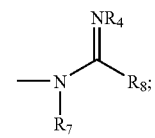

wherein:
$R_4$, $R_7$, and $R_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_8$ is

wherein:
$R_9$ and $R_{10}$ are each independently selected from the group consisting of H, alkyl, aryl, and
wherein:
$R_{11}$ is selected from the group consisting of H, alkyl, and aryl.

41. The pharmaceutically acceptable salt of claim 40, wherein the salt is a hydrochloride salt.

42. A pharmaceutical formulation comprising:
(a) a pharmaceutically acceptable carrier; and
(b) a compound of Formula I:

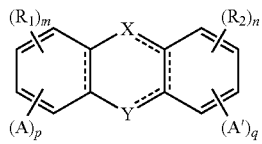

wherein:
X and Y are each independently selected from the group consisting of CH, CH$_2$, N, C=O, S, and NR$_3$,
wherein R$_3$ is selected from the group consisting of H, alkyl, aryl, alkoxyl, and aryloxyl, and
Y can be present or absent, and when absent, is replaced by a direct bond;
R$_1$ and R$_2$ are each independently selected from the group consisting of H, alkyl, halo, hydroxyl, alkoxyl, aryloxyl, and aralkyloxyl;
m and n are integers from 0 to 3;
p and q are each 1;
A and A' are each

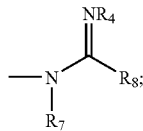

wherein:
R$_4$, R$_7$, and R$_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
R$_8$ is

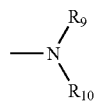

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl;

or a pharmaceutically acceptable salt thereof.

43. The formulation of claim 42, wherein:
X is CH$_2$; and
Y is absent.

44. The formulation of claim 43, wherein R$_8$ is selected from the group consisting of aryl and

wherein:
R$_9$ and R$_{10}$ are each independently selected from the group consisting of H, alkyl, aryl, and —OR$_{11}$;
wherein:
R$_{11}$ is selected from the group consisting of H, alkyl, and aryl.

45. The formulation of claim 44, wherein:
m and n are both zero; and
R$_7$ is H.

46. The formulation of claim 45, wherein:
R$_4$ is H; and
R$_8$ is phenyl.

47. The formulation of claim 45, wherein:
R$_4$ is H; and
R$_8$ is 2-pyridyl.

48. The formulation of claim 45, wherein R$_8$ is

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl.

49. The formulation of claim 48, wherein R$_4$ and R$_9$ are each H.
50. The formulation of claim 49, wherein R$_{10}$ is H.
51. The formulation of claim 49, wherein R$_{10}$ is methyl.
52. The formulation of claim 49, wherein R$_{10}$ is isopropyl.
53. The formulation of claim 49, wherein R$_{10}$ is methoxyl.
54. The formulation of claim 49, wherein R$_{10}$ is iso-butoxyl.
55. The formulation of claim 48, wherein:
R$_4$ is ethoxycarbonyl; and
R$_9$ is H.
56. The formulation of claim 55, wherein R$_{10}$ is H.
57. The formulation of claim 55, wherein R$_{10}$ is methyl.
58. The formulation of claim 55, wherein R$_{10}$ is isopropyl.
59. The formulation of claim 55, wherein R$_{10}$ is methoxyl.
60. The formulation of claim 55, wherein R$_{10}$ is iso-butoxyl.
61. The formulation of claim 42, wherein:
X is C=O; and
Y is absent.
62. The formulation of claim 61, wherein R$_8$ is selected from the group consisting of aryl and

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl.

63. The formulation of claim 62, wherein:
m and n are both zero; and
R$_7$ is H.

64. The formulation of claim 63, wherein R$_8$ is

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl.

65. The formulation of claim 64, wherein R$_9$ and R$_{10}$ are both H.

66. The formulation of claim 65, wherein R$_4$ is H.

67. The formulation of claim 65, wherein R$_4$ is ethoxycarbonyl.

68. The formulation of claim 42 wherein:
X and Y are both C=O.

69. The formulation of claim 68, wherein R$_8$ is selected from the group consisting of aryl and

wherein:
R$_9$ and R$_{10}$ are each independently selected from the group consisting of H, alkyl, aryl, and —OR$_{11}$;
wherein:
R$_{11}$ is selected from the group consisting of H, alkyl, and aryl.

70. The formulation of claim 69, wherein:
m and n are both zero; and
R$_7$ is H.

71. The formulation of claim 70, wherein R$_8$ is

wherein:
R$_9$ and R$_{10}$ are each independently selected from the group consisting of H, alkyl, aryl, and —OR$_{11}$;
wherein:
R$_{11}$ is selected from the group consisting of H, alkyl, and aryl.

72. The formulation of claim 71, wherein R$_9$ and R$_{10}$ are both H.

73. The formulation of claim 72, wherein R$_4$ is H.

74. The formulation of claim 42, wherein:
X is N; and
Y is CH.

75. The formulation of claim 74, wherein R$_8$ is selected from the group consisting of aryl and

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl.

76. The formulation of claim 75, wherein:
m and n are both zero; and
R$_7$ is H.

77. The formulation of claim 76, wherein R$_8$ is

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl.

78. The formulation of claim 77, wherein R$_9$ and R$_{10}$ are both H.

79. The formulation of claim 78, wherein R$_4$ is H.

80. The formulation of claim 42, wherein the compound is selected from the group consisting of:
2,7-bis-guanidino-9H-fluorene;
2,7-bis-guanidinofluoren-9-one;
2,7-bis-guanidinoanthraquinone;
3,6-bis-guanidinoacridine;
2,7-bis-(N"-ethoxycarbonyl)guanidino-9H-fluorene;
2,7-bis(N"-ethoxycarbonyl)guanidinofluoren-9-one;
2,7-bis(N"-ethoxycarbonyl-N'-methyl)guanidino-9H-fluorene;
2,7-bis(N"-ethoxycarbonyl-N'-isopropyl)guanidino-9H-fluorene;
2,7-bis(N"-ethoxycarbonyl-N'-methoxy)guanidino-9H-fluorene;
2,7-bis(N"-ethoxycarbonyl-N'-isobutoxy)guanidine-9H-fluorene;
2,7-bis(N"-methyl)guanidino-9H-fluorene;
2,7-bis(N'-iso-propyl)guanidino-9H-fluorene;
2,7-bis(N'-methoxy)guanidino-9H-fluorene;
2,7-bis(N'-isobutoxy)guanidine-9H-fluorene;
2,7-bis[(phenylimino)amino)]-9H-fluorene; and
2,7-bis[(2-pyridylimino)amino)-9H-fluorene.

81. A method of treating microbial infection in a subject in need thereof, the method comprising administering to the subject an effective amount of a compound of Formula I:

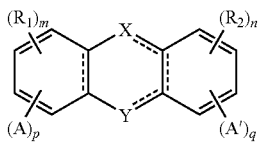

wherein:
X and Y are each independently selected from the group consisting of CH, CH$_2$, N, C=O, S, and NR$_3$,
wherein R$_3$ is selected from the group consisting of H, alkyl, aryl, alkoxyl, and aryloxyl, and
Y can be present or absent, and when absent, is replaced by a, direct bond;
R$_1$ and R$_2$ are each independently selected from the group consisting of H, alkyl, halo, hydroxyl, alkoxyl, aryloxyl, and aralkyloxyl;
m and n are integers from 0 to 3;
p and q are each 1;
A and A' are each

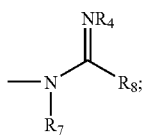

wherein:
R$_4$, R$_7$, and R$_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
R$_8$ is

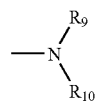

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl;
or a pharmaceutically acceptable salt thereof.

82. The method of claim 81, wherein:
X is CH$_2$; and
Y is absent.

83. The method of claim 82, wherein R$_8$ is selected from the group consisting of aryl and

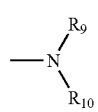

wherein:
R$_9$ and R$_{10}$ are each independently selected from the group consisting of H, alkyl, aryl, and —OR$_{11}$;
wherein:
R$_{11}$ is selected from the group consisting of H, alkyl, and aryl.

84. The method of claim 83, wherein:
m and n are both zero; and
R$_7$ is H.

85. The method of claim 84, wherein:
R$_4$ is H; and
R$_8$ is phenyl.

86. The method of claim 84, wherein:
R$_4$ is H; and
R$_8$ is 2-pyridyl.

87. The method of claim 84, wherein R$_8$ is

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl.

88. The method of claim 87, wherein R$_4$ and R$_9$ are each H.
89. The method of claim 88, wherein R$_{10}$ is H.
90. The method of claim 88, wherein R$_{10}$ is methyl.
91. The method of claim 88, wherein R$_{10}$ is isopropyl.
92. The method of claim 88, wherein R$_{10}$ is methoxyl.
93. The method of claim 88, wherein R$_{10}$ is iso-butoxyl.
94. The method of claim 87, wherein:
R$_4$ is ethoxycarbonyl; and
R$_9$ is H.
95. The method of claim 94, wherein R$_{10}$ is H.
96. The method of claim 94, wherein R$_{10}$ is methyl.
97. The method of claim 94, wherein R$_{10}$ is isopropyl.
98. The method of claim 94, wherein R$_{10}$ is methoxyl.
99. The method of claim 94, wherein R$_{10}$ is iso-butoxyl.
100. The method of claim 81, wherein:
X is C=O; and
Y is absent.
101. The method of claim 100, wherein R$_8$ is selected from the group consisting of aryl and

wherein:
R$_9$ and R$_{10}$ are each independently selected from the group consisting of H, alkyl, aryl, and —OR$_{11}$; and
wherein:
R$_{11}$ is selected from the group consisting of H, alkyl, and aryl.

102. The method of claim 101, wherein:
m and n are both zero; and
R$_7$ is H.

103. The method of claim 102, wherein $R_8$ is

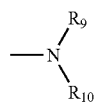

wherein:
$R_9$ and $R_{10}$ are each independently selected from the group consisting of H, alkyl, aryl, and —$OR_{11}$;
wherein:
$R_{11}$ is selected from the group consisting of H, alkyl, and aryl.

104. The method of claim 103, wherein $R_9$ and $R_{10}$ are both H.

105. The method of claim 104, wherein $R_4$ is H.

106. The method of claim 104, wherein $R_4$ is ethoxycarbonyl.

107. The method of claim 81 wherein:
X and Y are both C=O.

108. The method of claim 107, wherein $R_8$ is selected from the group consisting of aryl and

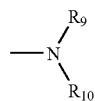

wherein:
$R_9$ and $R_{10}$ are each independently selected from the group consisting of H, alkyl, aryl, and —$OR_{11}$;
wherein:
$R_{11}$ is selected from the group consisting of H, alkyl, and aryl.

109. The method of claim 108, wherein:
m and n are both zero; and
$R_7$ is H.

110. The method of claim 109, wherein $R_8$ is

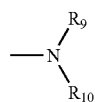

wherein:
$R_9$ and $R_{10}$ are each independently selected from the group consisting of H, alkyl, aryl, and —$OR_{11}$,
wherein:
$R_{11}$ is selected from the group consisting of H, alkyl, and aryl.

111. The method of claim 110, wherein $R_9$ and $R_{10}$ are both H.

112. The method of claim 111, wherein $R_4$ is H.

113. The method of claim 81, wherein:
X is N; and
Y is CH.

114. The method of claim 113, wherein $R_8$ is selected from the group consisting of aryl and

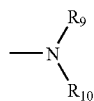

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

115. The method of claim 114, wherein:
m and n are both zero; and
$R_7$ is H.

116. The method of claim 115, wherein $R_8$ is

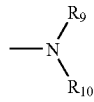

wherein:
$R_9$ and $R_{10}$ are each independently selected from the group consisting of H, alkyl, aryl, and —$OR_{11}$; and
wherein:
$R_{11}$ is selected from the group consisting of H, alkyl, and aryl.

117. The method of claim 116, wherein $R_9$ and $R_{10}$ are both H.

118. The method of claim 117, wherein $R_4$ is H.

119. The method of claim 81, wherein the compound is selected from the group consisting of:
2,7-bis-guanidino-9H-fluorene;
2,7-bis-guanidinofluoren-9-one;
2,7-bis-guanidinoanthraquinone;
3,6-bis-guanidinoacridine;
2,7-bis-(N''-ethoxycarbonyl)guanidino-9H-fluorene;
2,7-bis(N''-ethoxycarbonyl)guanidinofluoren-9-one;
2,7-bis(N''-ethoxycarbonyl-N'-methyl)guanidino-9H-fluorene;
2,7-bis(N''-ethoxycarbonyl-N'-isopropyl)guanidino-9H-fluorene;
2,7-bis(N''-ethoxycarbonyl-N'-methoxy)guanidino-9H-fluorene;
2,7-bis(N''-ethoxycarbonyl-N'-isobutoxy)guanidine-9H-fluorene;
2,7-bis(N'-methyl)guanidino-9H-fluorene;
2,7-bis(N'-iso-propyl)guanidino-9H-fluorene;
2,7-bis(N'-methoxy)guanidino-9H-fluorene;
2,7-bis(N'-isobutoxy)guanidine-9H-fluorene;
2,7-bis[(phenylimino)amino)]-9H-fluorene; and
2,7-bis[(2-pyridylimino)amino)-9H-fluorene.

120. The method of claim 81, wherein the compound of Formula I is administered in the form of a pharmaceutically acceptable salt.

121. The method of claim 120, wherein the pharmaceutically acceptable salt is a hydrochloride salt.

122. The method of claim 81, wherein the microbial infection is selected from one of a *Trypanosoma brucei rhodesiense* infection and a *Plasmodium falciparum* infection.

* * * * *